United States Patent
Hedrick et al.

(10) Patent No.: US 10,576,186 B2
(45) Date of Patent: Mar. 3, 2020

(54) ANTI-MICROBIAL DEVICE AND METHOD FOR ITS MANUFACTURE

(71) Applicant: NANOVIS, LLC, Columbia City, IN (US)

(72) Inventors: Matthew Hedrick, Carmel, IN (US); Chang Yao, West Lafayette, IN (US)

(73) Assignee: NANOVIS, LLC, Columbia City, IN (US)

(*) Notice: Subject to any disclaimer, the term of this patent is extended or adjusted under 35 U.S.C. 154(b) by 352 days.

(21) Appl. No.: 15/276,048

(22) Filed: Sep. 26, 2016

(65) Prior Publication Data

US 2017/0007743 A1  Jan. 12, 2017
US 2017/0296702 A9  Oct. 19, 2017

Related U.S. Application Data

(63) Continuation of application No. PCT/US2015/022743, filed on Mar. 26, 2015.

(60) Provisional application No. 61/970,501, filed on Mar. 26, 2014.

(51) Int. Cl.

| | |
|---|---|
| *A61L 27/54* | (2006.01) |
| *C23C 22/05* | (2006.01) |
| *C25D 11/02* | (2006.01) |
| *C23C 22/78* | (2006.01) |
| *A61L 27/04* | (2006.01) |
| *A61L 27/30* | (2006.01) |
| *C25D 11/26* | (2006.01) |
| *C25D 11/34* | (2006.01) |
| *C09D 1/00* | (2006.01) |
| *C09D 7/61* | (2018.01) |
| *C04B 35/447* | (2006.01) |
| *C04B 35/622* | (2006.01) |
| *C09D 5/14* | (2006.01) |

(52) U.S. Cl.
CPC .............. *A61L 27/54* (2013.01); *A61L 27/04* (2013.01); *A61L 27/306* (2013.01); *C04B 35/447* (2013.01); *C04B 35/62222* (2013.01); *C09D 1/00* (2013.01); *C09D 5/14* (2013.01); *C09D 7/61* (2018.01); *C23C 22/05* (2013.01); *C23C 22/78* (2013.01); *C25D 11/02* (2013.01); *C25D 11/26* (2013.01); *C25D 11/34* (2013.01); *A61L 2202/21* (2013.01); *A61L 2300/102* (2013.01); *A61L 2300/104* (2013.01); *A61L 2300/404* (2013.01); *A61L 2300/61* (2013.01); *A61L 2400/12* (2013.01); *A61L 2420/02* (2013.01); *C04B 2235/447* (2013.01)

(58) Field of Classification Search
CPC .......... A61L 27/54; A61L 27/04; C23C 22/05; C23C 22/78; C04B 35/447; C09D 1/00; C25D 11/26
USPC ........................................................ 428/469
See application file for complete search history.

(56) References Cited

U.S. PATENT DOCUMENTS

| | | | |
|---|---|---|---|
| 2009/0093881 A1 | 4/2009 | Bandyopadhyay et al. | |
| 2009/0304761 A1 | 12/2009 | Rabiei | |
| 2011/0014258 A1* | 1/2011 | Gan ........................ | A61L 27/30 424/409 |
| 2011/0014285 A1 | 1/2011 | Gan et al. | |
| 2011/0125263 A1* | 5/2011 | Webster ................ | A61L 27/306 623/11.11 |
| 2012/0276336 A1 | 11/2012 | Malshe et al. | |
| 2013/0238085 A1 | 9/2013 | Nabutovsky et al. | |

FOREIGN PATENT DOCUMENTS

| | | |
|---|---|---|
| WO | 2009095705 A2 | 8/2009 |
| WO | 2013040208 A1 | 3/2013 |

OTHER PUBLICATIONS

Extended European Search Report and European Search Opinion issued in European Patent Application No. 15769574.3 dated Sep. 20, 2017.

International Search Report and Written Opinion of the Searching Authority regarding PCT Application No. PCT/US2015/022743 dated Jun. 25, 2015.

* cited by examiner

*Primary Examiner* — Doris L Lee
(74) *Attorney, Agent, or Firm* — Heslin Rothenberg Farley & Mesiti P.C.

(57) ABSTRACT

An antimicrobial medical device that includes a substrate having a metal surface that is made from a metal or metal alloy that may include stainless steel, cobalt, and titanium. Disposed on the metal surface is a first antimicrobial oxide layer that includes an antimicrobial metal that may include silver, copper, and zinc, and combinations thereof. The atoms of antimicrobial metal in the first antimicrobial oxide layer are of a first concentration. The first antimicrobial oxide layer is positioned in a direction opposite that of the metal surface. The device further includes a second antimicrobial oxide layer that includes an antimicrobial metal that may be silver, copper, and zinc, and combinations thereof. The atoms of the antimicrobial metal present in the second antimicrobial oxide layer are of a second concentration. The first concentration and the second concentration are not equal. Methods for making the antimicrobial medical device are also disclosed.

33 Claims, 18 Drawing Sheets

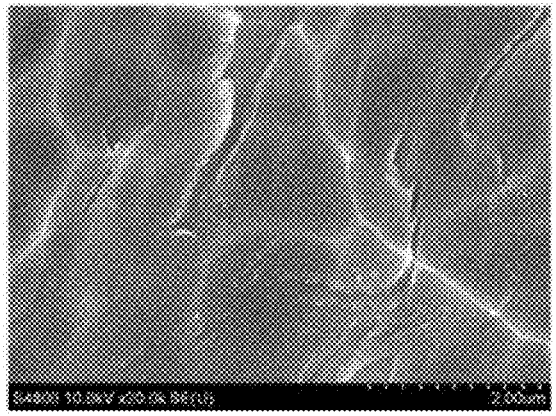 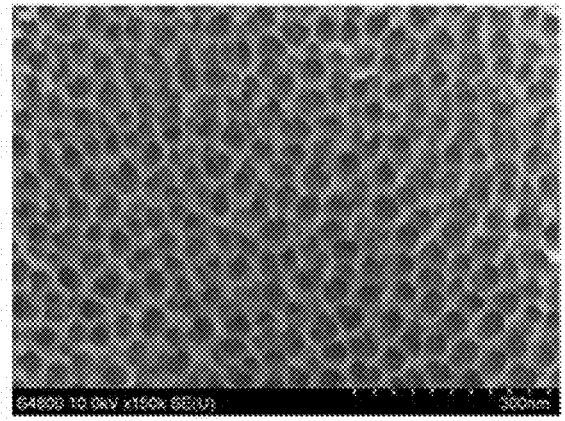
FIG. 8A  FIG. 8B
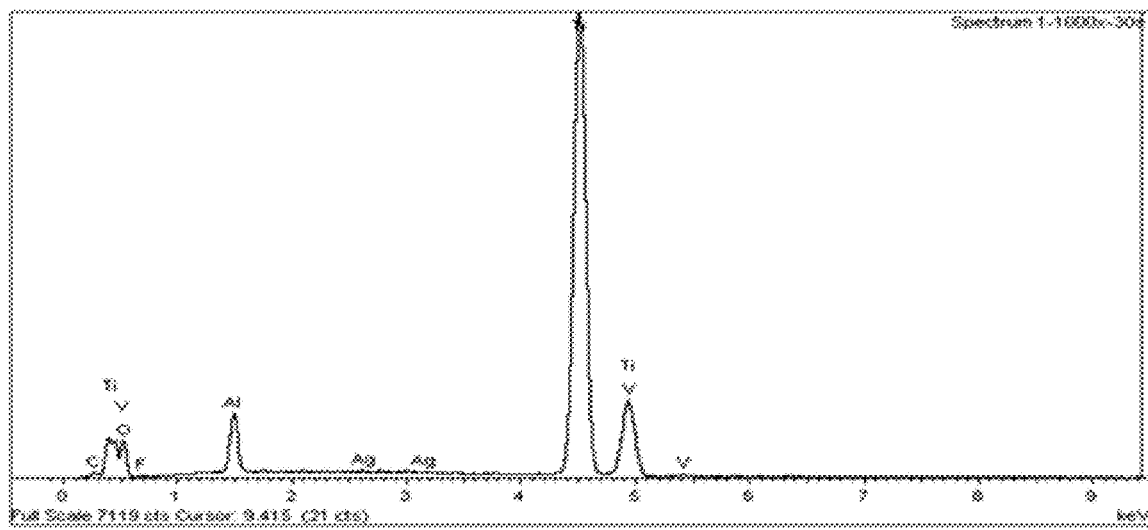
FIG. 8C

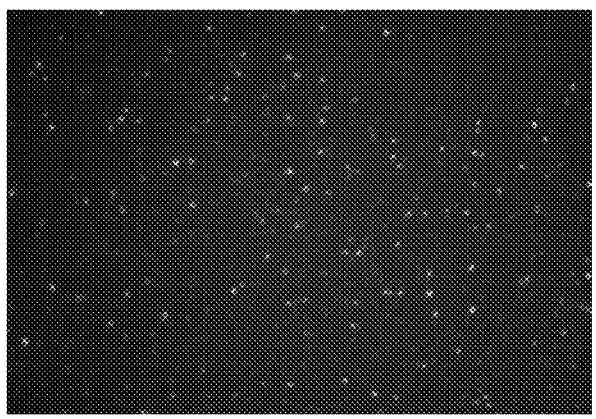 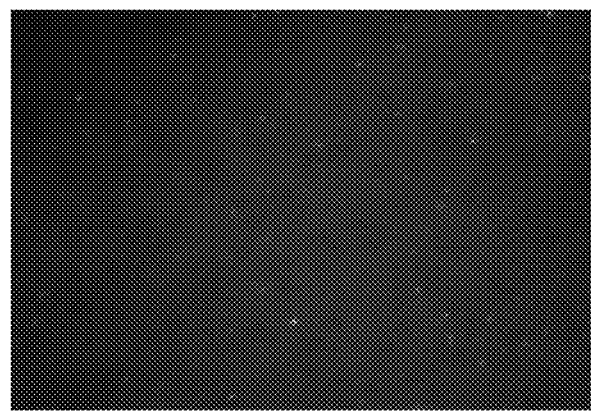
FIG. 10A                    FIG. 10B

ANTI-MICROBIAL DEVICE AND METHOD FOR ITS MANUFACTURE

CROSS-REFERENCE TO RELATED APPLICATIONS

This application is a continuation of PCT Application No. PCT/US2015/022743 filed on Mar. 26, 2015 which claims priority to U.S. Provisional Application No. 61/970,501, filed on Mar. 26, 2014, each of which is herein incorporated by reference in its entirety.

FIELD OF THE INVENTION

The present invention generally relates to a medical device having antimicrobial properties, and to a method of fabricating the medical device.

BACKGROUND OF THE INVENTION

Infection is one of the most serious complications for medical devices, including implants. Efforts to rectify this problem have included surface-treatment with coatings that prevent bacterial adhesion, but such coatings typically are of limited effectiveness.

Surgical Site Infections (SSIs) involving medical devices (e.g., orthopedic implants) are a well-known, widespread and severe problem leading to significant patient morbidity and mortality. Medical devices often serve as a nidus for bacterial colonization and biofilms that trigger the formation of fibrous tissue around infected devices instead of bone. This scenario further complicates patient outcomes by degrading bone and decreasing the device fixation required to stabilize the segment (which is often the primary objective of the original surgery). Yet, the need to maintain the stability of the implant-bone interface makes leaving the device in place and attempting to treat the infection with, e.g., irrigation, debridement(s) and/or antibiotics the standard of care for many procedures, such as common spinal fusions.

Thus, a need exists for technology that addresses the problems of colonizing bacteria (preventing biofilm formation), and that, in some cases, also allows for the simultaneous and expeditious formation of a strong bone-to-implant interface that achieves construct stability.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

Briefly, the present invention satisfies the need for an antimicrobial medical device and method of making the same that address the problem of colonizing bacteria. Some embodiments of the invention also allow for controlled antimicrobial release, and/or for the simultaneous and expeditious formation of a strong bone-to-implant interface that achieves construct stability.

In a first aspect, the invention provides an antimicrobial medical device comprising:
a substrate comprising a metal surface, said metal surface comprising atoms of at least one of a metal or metal alloy comprising one or more of stainless steel, cobalt, and titanium;
on the metal surface, a first antimicrobial oxide layer comprising atoms of the metal or metal alloy and atoms of an antimicrobial metal selected from the group consisting of silver, copper, and zinc, and combinations thereof, the atoms of antimicrobial metal being present in the first antimicrobial oxide layer in a first concentration; and
on the first antimicrobial oxide layer, positioned in a direction opposite that of the metal surface, a second antimicrobial oxide layer comprising atoms of an antimicrobial metal selected from the group consisting of silver, copper, and zinc, and combinations thereof, the atoms of antimicrobial metal being present in the second antimicrobial oxide layer in a second concentration,
wherein the first concentration is not equal to the second concentration.

In a second aspect, the invention provides a method for making an antimicrobial medical device, said method comprising:
providing a substrate comprising a metal surface, said metal surface comprising atoms of at least one of a metal or metal alloy comprising one or more of stainless steel, cobalt, and titanium;
forming, on the metal surface, a first antimicrobial oxide layer comprising atoms of the metal or metal alloy and atoms of an antimicrobial metal selected from the group consisting of silver, copper, and zinc, and combinations thereof, the atoms of antimicrobial metal being present in the first antimicrobial oxide layer in a first concentration; and
forming, on the first antimicrobial oxide layer, positioned in a direction opposite that of the metal surface, a second antimicrobial oxide layer comprising atoms of an antimicrobial metal selected from the group consisting of silver, copper, and zinc, and combinations thereof, the atoms of antimicrobial metal being present in the second antimicrobial oxide layer in a second concentration,
wherein the first concentration is not equal to the second concentration.

The present invention may address one or more of the problems and deficiencies of the art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

Certain embodiments of the presently-disclosed antimicrobial medical devices and methods for making the same have several features, no single one of which is solely responsible for their desirable attributes. Without limiting the scope of these devices and methods as defined by the claims that follow, their more prominent features will now be discussed briefly. After considering this discussion, and particularly after reading the section of this specification entitled "Detailed Description of the Invention," one will understand how the features of the various embodiments disclosed herein provide a number of advantages over the current state of the art. These advantages may include, without limitation: providing devices that utilize a multi-layer antimicrobial loading that affectively addresses the problem of infection, as it occurs in relation to medical devices, including over prolonged periods of time; providing microbicidal technology to reduce colonizing bacteria; providing devices that are osteoinductive even in the presence of bacteria; and providing devices that rapidly achieve fixation of bone segment to stabilize the bone-device (e.g., bone-implant structure). Embodiments of the inventive antimicrobial medical devices and methods of forming the same have widespread clinical relevance and applicability, including, but not limited to spine, trauma, dental, and other applications.

These and other features and advantages of this invention will become apparent from the following detailed description of the various aspects of the invention taken in conjunction with the appended claims and the accompanying drawings.

BRIEF DESCRIPTION OF THE DRAWINGS

The present invention will hereinafter be described in conjunction with the following drawing figures, wherein like numerals denote like elements, and:

FIGS. 8A-C provide SEM and EDS image data relating to structural features and the chemical makeup of a nanofunctionalized device according to methods discussed herein, having a first antimicrobial oxide layer;

FIGS. 10A and 10B are photomicrographs that show *S. sureus* growth on anodized Ti-6Al-4V in the absence of antimicrobial treatment (control) (FIG. 10A) and on anodized Ti-6Al-4V that has been soaked for approximately 30 minutes in an [Ag(NH$_3$)$_2$]NO$_3$ solution (FIG. 10B);

DETAILED DESCRIPTION OF THE INVENTION

Figure 1A:
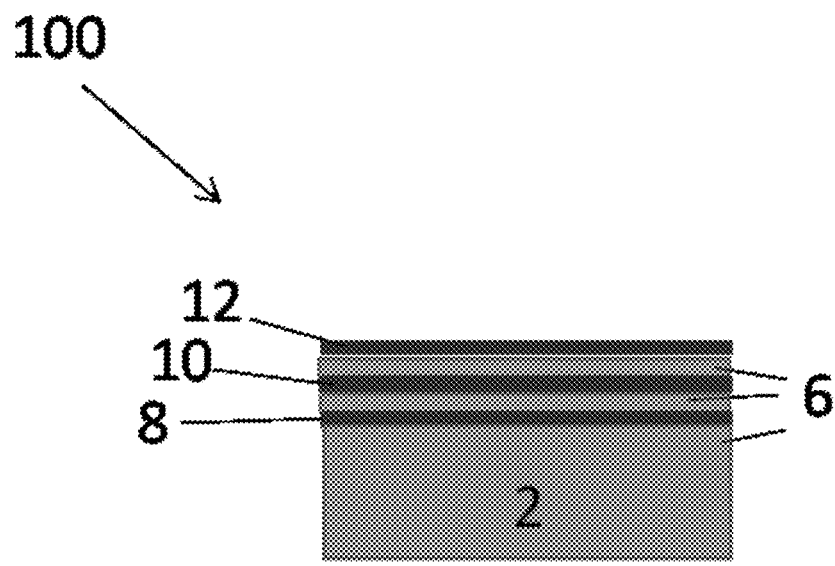
FIGS. 1A and 1B are schematics depicting the first and second antimicrobial oxide layers on metal surfaces according to certain embodiments of the invention.

Aspects of the present invention and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure.

Reference is made below to the drawings, which are not necessarily drawn to scale for ease of understanding, wherein the same reference numerals retain their designation and meaning for the same or like elements throughout the various drawings.

In a first aspect, the invention provides an antimicrobial medical device comprising:
  a substrate comprising a metal surface, said metal surface comprising atoms of at least one of a metal or metal alloy comprising one or more of stainless steel, cobalt, and titanium;
  on the metal surface, a first antimicrobial oxide layer comprising atoms of the metal or metal alloy and atoms of an antimicrobial metal selected from the group consisting of silver, copper, and zinc, and combinations thereof, the atoms of antimicrobial metal being present in the first antimicrobial oxide layer in a first concentration; and
  on the first antimicrobial oxide layer, positioned in a direction opposite that of the metal surface, a second antimicrobial oxide layer comprising atoms of an antimicrobial metal selected from the group consisting of silver, copper, and zinc, and combinations thereof, the atoms of antimicrobial metal being present in the second antimicrobial oxide layer in a second concentration, wherein the first concentration is not equal to the second concentration.

As used herein, when an element (e.g., a layer) is referred to as being "on" (e.g., deposited on, formed on, disposed on, etc.) or "over" another element, it can be directly on the other element or intervening elements may also be present. In contrast, when an element is referred to as being "directly" on or over another element, there are no intervening elements present.

As used herein, the term "medical device" refers to any type of device/appliance that is totally or partly introduced, surgically or medically, into a patient's body and which may remain there after a procedure or may be removed during treatment.

In some embodiments, the inventive antimicrobial medical device is a device used for spine, trauma, or dental applications. In some embodiments, the antimicrobial medical device is a medical implant. For example, in certain embodiments, the medical device is an implant selected from an orthopedic implant and a neurosurgical implant.

Embodiments of antimicrobial medical devices according to the invention have microbicidal properties, due to the inclusion of at least the first and second antimicrobial oxide layers. As discussed in greater detail below, it has been found that the multilayer antimicrobial loading approach used in the invention provides embodiments that are effective in reducing colonizing bacteria, while simultaneously offering osteoinductive properties that allow for rapid bone growth despite the presence of bacteria. This is particularly advantageous in view of the fact that often, when a medical device is used, the device serves, within a patient, as a nidus for bacterial colonization and biofilms that trigger the formation of fibrous tissue around infected devices instead of bone, thereby resulting not only in infection, but also in conditions that degrade bone and prevent proper device fixation within the patient. Accordingly, embodiments of the inventive antimicrobial medical device allow for improved patient outcomes via the reduction or prevention of infection, and by allowing proper device fixation and stabilization within the patient.

The inventive antimicrobial metal device includes a substrate, which comprises a metal surface. The metal surface comprises atoms of at least one of a metal or metal alloy, the metal or metal alloy comprising one or more of stainless steel, cobalt, and titanium. Accordingly, the metal surface includes atoms from at least one of stainless steel, cobalt, and titanium.

In some embodiments, the metal surface comprises titanium. For example, in some embodiments, the metal surface is fabricated of commercially pure (CP) titanium. In some embodiments, the metal surface comprises a metal alloy. In particular embodiments, the metal alloy comprises one or more of stainless steel, a titanium alloy (e.g., Ti6Al4V or nitinol), and a cobalt-chrome alloy.

In some embodiments, the metal surface is fabricated of, or consists essentially of, CP titanium, stainless steel, a titanium alloy, or a cobalt-chrome alloy.

In a particular embodiment, the metal surface is Ti6Al4V.

In some embodiments, the metal surface is nonporous, whereas in other embodiments, the metal surface is porous.

The inventive medical device includes, disposed on the metal surface, a first antimicrobial oxide layer comprising atoms of the metal or metal alloy and atoms of an antimicrobial metal selected from the group consisting of silver, copper, and zinc, and combinations thereof.

In various embodiments, the atoms of the antimicrobial metal are metal ions (e.g., silver, copper, or zinc ions) that bind ionically to an oxidized surface or other portion of the medical device. If desired, in some embodiments, the metal ion may be subsequently reduced.

The ionic binding of the antimicrobial metal to an oxidized surface results in the formation of a mixed oxide. For such embodiments, in the case of the first antimicrobial oxide layer, a mixed oxide may be formed between the oxygen atom of an oxidized device surface or layer/structure (e.g., the oxidized metal surface) and an antimicrobial metal atom/ion. For example, in some embodiments, the first antimicrobial oxide layer comprises oxidized titanium. In non-limiting embodiments, said oxidized titanium may be naturally oxidized titanium, heat oxidized titanium, electrochemically treated titanium, etched titanium, or nano-anodized titanium. The oxidized titanium acts as a reservoir for ionic antimicrobial agents, which can bind ionically to the oxygen in the titanium oxide, thereby forming a mixed oxide that comprises oxygen bound to the atom of the oxidized metal surface (e.g., Ti), and to the antimicrobial atom (e.g., ionic silver). For example, in some embodiments, ionic silver, e.g., from an aqueous $[Ag(NH_3)_2]NO_3$ solution, binds ionically to, and is stored on an oxidized titanium-comprising surface via the mechanism below:

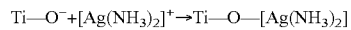

$Ti-O^- + [Ag(NH_3)_2]^+ \rightarrow Ti-O-[Ag(NH_3)_2]$

Persons having ordinary skill in the art will appreciate that the above mechanism also supports binding to other metal oxides, and would be equally applicable using other cations comprising antimicrobial atoms (e.g., cations comprising silver, copper, and/or zinc).

In some embodiments, the first antimicrobial oxide layer comprises atoms of titanium or chromium (i.e., comprises atoms of at least one of titanium and chromium).

In some embodiments, the first antimicrobial oxide layer comprises, as the atoms of the antimicrobial metal, at least one of silver ions, copper ions, and zinc ions.

In particular embodiments, the first antimicrobial oxide layer comprises silver atoms.

The atoms of the antimicrobial metal are present in the first antimicrobial oxide layer in a first concentration. Examples of acceptable methods for antimicrobial loading are discussed below. Persons having ordinary skill in the art will understand that the desired concentration of antimicrobial atoms in the antimicrobial oxide layers may vary depending on the intended device and its application. Nonetheless, in some non-limiting embodiments, the first concentration ranges from 0.5 to 60 µg of antimicrobial atoms per cm$^2$ (e.g., 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 µg/cm$^2$), including any and all ranges and subranges therein (e.g., 0.5 to 25 µg/cm$^2$).

In some embodiments, the first antimicrobial oxide layer does not comprise silicon.

In some embodiments, the first antimicrobial oxide layer does not comprise a ceramic material.

In some embodiments, the first antimicrobial oxide layer does not comprise, and is not in direct contact with, zeolite.

In some embodiments, the first antimicrobial oxide layer is nonporous, whereas in other embodiments, the first antimicrobial oxide layer is porous.

The inventive antimicrobial medical device also includes, on the first antimicrobial oxide layer, positioned in a direction opposite that of the metal surface, a second antimicrobial oxide layer. The second antimicrobial oxide layer also comprises atoms of an antimicrobial metal selected from the group consisting of silver, copper, and zinc, and combinations thereof, which are present in the second antimicrobial oxide layer in a second concentration.

In various embodiments, the atoms of the antimicrobial metal are metal ions (e.g., silver, copper, or zinc ions) that bind ionically to an oxidized surface or other portion of the medical device. If desired, in some embodiments, the metal ion may be subsequently reduced.

As in certain embodiments of the first antimicrobial oxide layer, in the case of certain embodiments of the second antimicrobial oxide layer, the ionic binding of the antimicrobial metal to an oxidized surface results in the formation of a mixed oxide. For such embodiments, a mixed oxide may be formed between the oxygen atom of an oxidized device surface or layer/structure and an antimicrobial metal atom/ion. For example, in some embodiments, the second antimicrobial oxide layer comprises oxidized titanium. In non-limiting embodiments, said oxidized titanium may be naturally oxidized titanium, heat oxidized titanium, electrochemically treated titanium, etched titanium, or nano-anodized titanium (e.g., in fluorine-containing electrolyte). The oxidized titanium acts as a reservoir for ionic antimicrobial agents, which can bind ionically to the oxygen in the titanium oxide, thereby forming a mixed oxide that comprises oxygen bound to the atom of the oxidized metal surface (e.g., Ti), and to the antimicrobial atom (e.g., ionic silver).

In some embodiments, the second antimicrobial oxide layer comprises atoms of titanium or chromium (i.e., comprises atoms of at least one of titanium and chromium).

In some embodiments, the second antimicrobial oxide layer comprises, as the atoms of the antimicrobial metal, at least one of silver ions, copper ions, and zinc ions.

In some embodiments, the second antimicrobial oxide layer comprises a mixed oxide that contains atoms of at least one of stainless steel, cobalt, and titanium.

In particular embodiments, the second antimicrobial oxide layer comprises silver atoms.

The atoms of the antimicrobial metal are present in the second antimicrobial oxide layer in a second concentration, which is different from the first concentration. In some non-limiting embodiments, the second concentration ranges from 0.5 to 60 μg of antimicrobial atoms per $cm^2$ (e.g., 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 μg/$cm^2$), including any and all ranges and subranges therein (e.g., 5 to 25 μg/$cm^2$), with the proviso that the second concentration does not equal the first concentration.

In some embodiments, the first and or second oxide layer has a thickness of about 100 nm to 3 μm (e.g., 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1500, 2000, 2500, or 3000 nm), including any and all ranges and subranges therein.

In some embodiments, the second concentration is less than the first concentration.

In other embodiments, the second concentration is greater than the first concentration.

In some embodiments, there is at least a 10% difference between the first concentration and the second concentration $$\left( \text{i.e.,} \ \frac{|(\text{first concentration}) - (\text{second concentration})|}{\text{first concentration}} \times 100\% \geq 10\% \right).$$

The concentration of the atoms of antimicrobial metal in the first and second antimicrobial oxide layers can be carefully controlled and is below concentrations that would cause dangerous toxicological side effects. In various embodiments, the antimicrobial release profile (e.g., of silver ions, or of whatever other antimicrobial atoms are used) is controlled by different binding and/or loading (e.g., antimicrobial layering) strategies.

In some embodiments, the second antimicrobial oxide layer does not comprise silicon.

In some embodiments, the second antimicrobial oxide layer does not comprise a ceramic material.

In some embodiments, the second antimicrobial oxide layer does not comprise, and is not in direct contact with, zeolite.

In some embodiments, the second antimicrobial oxide layer is nonporous, whereas in other embodiments, the second antimicrobial oxide layer is porous.

In some embodiments, the second antimicrobial oxide layer is disposed directly on the first antimicrobial oxide layer (i.e., the layers are in direct contact with one another).

In various embodiments, the layering (i.e., the at least first and second antimicrobial oxide layers) provides an antimicrobial medical device that is configured to allow for controllable sustained release of antimicrobial agent.

In some embodiments, for example, in embodiment 100 of FIG. 1A, the first antimicrobial oxide layer 8 and second antimicrobial oxide layer 10 are distinct layers separated from one another by at least an intermediate layer 6, which may be, e.g., porous by anodization, flat by deposition, etc. (i.e., the layers are not in direct contact with one another). In some embodiments, the intermediate layer 6 is fabricated from the same material as the metal surface. In other embodiments, the intermediate layer is fabricated from a different material than the metal surface. FIG. 1A includes an optional additional antimicrobial oxide layer 12, which is separated from the second antimicrobial oxide layer 10 by a second intermediate layer 6. In the depicted embodiment 100, the first antimicrobial oxide layer 8 is formed on titanium-comprising substrate 2.

In some embodiments, the intermediate layer comprises atoms of at least one of a metal or metal alloy comprising one or more of stainless steel, cobalt, and titanium.

In some embodiments, the intermediate layer does not comprise an antimicrobial metal selected from the group consisting of silver, copper, and zinc, and combinations thereof.

In some embodiments of the inventive antimicrobial medical device, the device comprises a plurality of nanostructures.

In some embodiments, the first and/or second antimicrobial oxide layers are contained within the plurality of nanostructures.

In some embodiments the nanostructures are disposed directly on the metal surface. In some embodiments, the nanostructures are disposed on a layer that is disposed on the metal surface.

While the nanostructures may be of any known geometry, in particular embodiments, the nanostructures are nanotubes.

In some embodiments, the nanostructures comprise titanium dioxide.

Figure 1B:
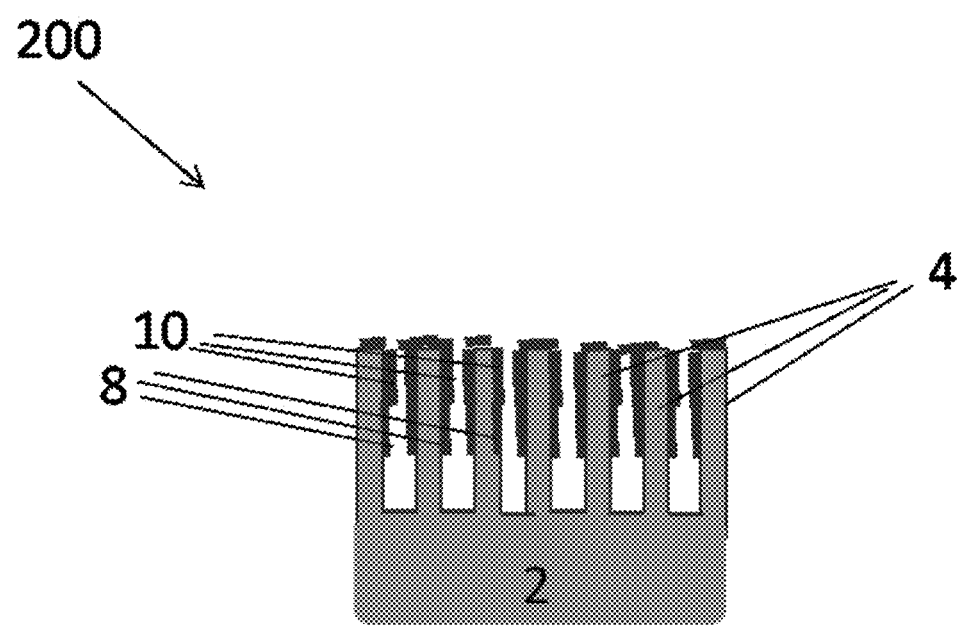
Figure 1C:
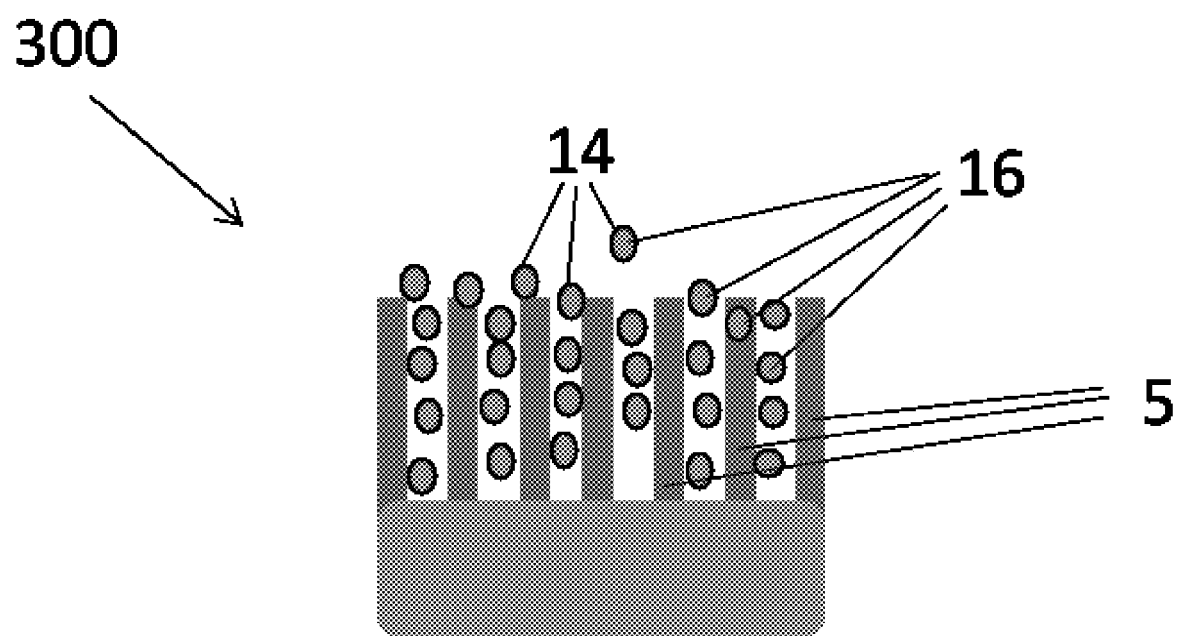
FIG. 1C is a comparative prior art schematic depicting alternatively loaded nanoparticles absorbed with Ag+, which are loaded to crystalline anatase $TiO_2$ not in accordance with the present invention.

In some embodiments, the nanostructures are amorphous non-crystalline nanostructures. For example, in some embodiments, the nanostructures comprise amorphous titanium dioxide (versus crystalline titanium dioxide such as, e.g., anatase). FIG. 1B depicts such an embodiment 200 wherein the first antimicrobial oxide layer 8 and second antimicrobial oxide layer 10 are contained within amorphous titanium dioxide nanotubes 4 that are formed on titanium-comprising substrate 2. The first and second antimicrobial oxide layers 8 and 10 are formed by loading ions (e.g., Ag+) directly to amorphous titanium dioxide nanotubes in a solution of silver ammonia nitrate. It is noted that the multi-layering embodiments of the present invention, such as that of FIG. 1B differ from, for example, embodiments described in EP 2495356, which do not use such a layering technique, and wherein, as shown in embodiment 300 of FIG. 1C, silver ions 14 are loaded to titanium dioxide nanoparticles 16, which are then loaded into annealed crystalline nanotubes 5.

In some embodiments, the inventive antimicrobial medical device further comprises a ceramic layer (e.g., calcium phosphate). In some embodiments, the ceramic layer comprises atoms of an antimicrobial metal selected from the group consisting of silver, copper, and zinc, and combinations thereof.

In some embodiments, the inventive antimicrobial medical device does not comprise a ceramic material disposed on (directly, or indirectly) the metal surface.

In some embodiments of the inventive antimicrobial medical device, the substrate comprises a body of a device, such as an implant. For example, in some embodiments, the metal surface is disposed on a substrate that comprises a metallic, ceramic, stainless steel, polymeric (e.g., polyetherether-ketone (PEEK)), or other implant. In some embodiments, the substrate is a three-dimensional structure.

In some embodiments, the inventive antimicrobial medical device has at least one of pico, micron, sub-micron, nano or meso-scale surface features, or a smooth surface (e.g., a smooth but porous surface), that facilitates tissue attachment and growth at an interface between the medical device and tissue or bone.

In a second aspect, the invention provides a method for making an antimicrobial medical device, said method comprising:
providing a substrate comprising a metal surface, said metal surface comprising atoms of at least one of a metal or metal alloy comprising one or more of stainless steel, cobalt, and titanium;
forming, on the metal surface, a first antimicrobial oxide layer comprising atoms of the metal or metal alloy and atoms of an antimicrobial metal selected from the group consisting of silver, copper, and zinc, and combinations thereof, the atoms of antimicrobial metal being present in the first antimicrobial oxide layer in a first concentration; and
forming, on the first antimicrobial oxide layer, positioned in a direction opposite that of the metal surface, a second antimicrobial oxide layer comprising atoms of an antimicrobial metal selected from the group consisting of silver, copper, and zinc, and combinations thereof, the atoms of antimicrobial metal being present in the second antimicrobial oxide layer in a second concentration,
wherein the first concentration is not equal to the second concentration.

The inventive methods of making an antimicrobial medical device may be used to fabricate the inventive antimicrobial medical device according to embodiments of the first aspect of the invention.

In some embodiments, at least one of forming the first antimicrobial oxide layer and forming the second antimicrobial oxide layer comprises exposing at least a portion of the device to a solution comprising an antimicrobial metal selected from the group consisting of silver, copper, and zinc, and combinations thereof, or to an antimicrobial metal ion thereof. Generally, the solution is a solution that comprises a solvent (e.g., water) and a soluble silver, copper, or zinc salt.

In some embodiments, "exposing at least a portion of the device" to the solution comprises exposing the metal surface and/or a portion of the device disposed, either directly or indirectly, on the metal surface, to the solution. For example, in some embodiments, the exposing comprises exposing nanostructures or a portion thereof to the solution. In some embodiments, both forming the first antimicrobial oxide layer and forming the second antimicrobial oxide layer comprises this exposing process.

In some embodiments, the solution comprises silver ions, copper ions, and/or zinc ions. In particular embodiments, the solution comprises silver or silver ions.

In some embodiments, the solution is made by dissolving a silver, copper, or zinc salt in solvent. In some embodiments, the solvent is water. In some embodiments, the solvent is water and the salt is a silver salt. In some embodiments, the silver salt is $[Ag(NH_3)_2]NO_3$.

In some embodiments, the first antimicrobial oxide layer is formed directly on the metal surface (i.e., in direct contact with the metal surface).

While oxide layers form naturally on various metal and metal alloy surfaces, there are also many known methods for forming (including enhancing) oxide layers. For the present invention, the first and second antimicrobial oxide layers may be formed by reacting a precursor oxide layer (whether a natural oxide layer or an otherwise formed or enhanced oxide layer) with antimicrobial atoms. While any art acceptable methods may be employed to form the oxide layer, including the precursor oxide layer, in some embodiments, forming the first and/or second antimicrobial oxide layer comprises mechanical roughening, heat treatment, acid etching, and/or electrochemical oxidization. In some embodiments, forming the first and/or second antimicrobial oxide layer comprises anodizing.

In some embodiments, forming the first antimicrobial oxide layer comprises heat treating the metal surface, acid etching the metal surface, or electrochemically oxidizing the metal surface. In some embodiments, forming the first antimicrobial oxide layer comprises anodizing the metal surface.

In some embodiments, forming the second antimicrobial oxide layer comprises depositing a metal (e.g., a metal layer or structure), on the first antimicrobial oxide layer, and forming the second antimicrobial oxide layer directly on the metal, either via reaction with a natural oxide on the metal, or by first applying an oxidizing treatment to a surface of the metal. While the metal layer or structure may be formed using any art-acceptable method, in some embodiments, it is spray-coated on the substrate (e.g., onto the metal surface or first antimicrobial oxide layer), formed using physical vapor deposition (PVD), for forming by anodizing.

In some embodiments, the inventive method comprises forming on the metal surface a plurality of nanostructures, which may optionally contain the first and second antimicrobial oxide layers. In some embodiments, the plurality of nanostructures are formed by anodizing. As will be appreciated by those skilled in the art, by varying anodization parameters, different structures with different sizes (nano or, in some embodiments, micron), morphologies, surface energies and other properties may be created.

In some embodiments, the nanostructures are nanotubes. In some embodiments, the nanotubes have an average diameter of less than or equal to 100 nm. In some embodiments, the nanotubes have an average diameter of 5 to 100 nm (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nm), including any and all ranges and subranges therein.

Nanotube length can easily be modified depending on the intended medical device and its application. While nanotubes of any desired length are encompassed by the invention, in some embodiments, the nanotubes have an average length ranging from 15 nm to several microns. In some embodiments, the nanotubes have an average length of 20 nm to 1,000 nm (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nm), including all ranges and subranges therein.

In some embodiments, the inventive method comprises forming nanostructures on the metal surface (e.g., by anodizing), then forming the first antimicrobial oxide layer, then, after forming the first antimicrobial oxide layer, further anodizing to continue to form the nanostructures, and subsequently forming the second antimicrobial oxide layer, which may be comprised within the nanostructures. By stopping and restarting the formation of nanostructures e.g., nanotubes) by anodization, the antimicrobial metal in solution can be modified to increase or decrease the amount or type of antimicrobial agent incorporated into the portion of the device being loaded with antimicrobial material. This allows for customized elution profiles to be created. In other embodiments, this effect may also be achieved by subjecting different portion(s) of the antimicrobial medical device to different loading conditions (e.g., a first part of the device may be soaked in antimicrobial solution, followed by a separate soak of a different part of the device, or of only a portion of the first part).

In some embodiments, the inventive method comprises a method of making an antimicrobial medical device that comprises a Ti-6Al-4V metal surface, wherein the first and second antimicrobial oxide layers are formed on titanium dioxide nanostructures. For example, in particular embodiments, substrates comprising anodized Ti-6Al-4V metal surfaces are thoroughly cleaned and dried to remove any surface contamination. During anodization, the anodized titanium substrates serve as anode in an electrochemical cell. An electrolyte is used, which can vary in composition and concentration. For example, in some embodiments, dilute hydrofluoric acid is used as an electrolyte. In some embodiments, the dilute HF electrolyte ranges from 0.25% to 1.5% HF, including any and all ranges and subranges therein.

During anodization, voltage is used as is known in the art. For example, in some embodiments, the voltage can vary from 2 to 45 V (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 V), including any and all ranges and subranges therein (e.g., from 5 to 20 V). Duration is controlled depending on the desired nanostructures to be form. For example, in some embodiments, the anodizing treatment ranges from 10 seconds to 20 minutes. The as-oxidized titanium may be soaked in an aqueous solution of $[Ag(NH_3)_2]NO_3$. In some embodiments, to prepare the solution, droplets of ammonia hydroxide are added into 20 wt % silver nitrate until precipitates all dissolve. The stock solution is further diluted to prepare 0.001M to 0.1 M working solution.

In some embodiments, soaking (in antimicrobial metal solution) is performed to form one or more antimicrobial oxide layers on the nanostructures. In some embodiments, the soaking process lasts from, e.g., 10 minutes to 24 hours. The soaking process may be one-time (single dose) or repeated (multiple dose). In some multi-dose embodiments, the substrates is rinsed with water thoroughly, completely dried in the air, and re-soaked in silver containing solution. In some embodiments, the soaking process may occur after the surface is fully oxidized. In this case, silver ions bind to layers of surface oxides and result in a relatively quick release profile.

In various embodiments, the soaking process may be performed repeatedly at different stages of oxidation process (heat treatment, anodization, or mixed). For example, a substrate may be first anodized for, e.g., 10 seconds, to initiate nanostructure (e.g., nanotube) formation. Then it may be soaked in silver solution to adsorb ionic silver. A heat treatment may be used to fuse the silver ions into the underlying surface but not change the nanotube morphology. Subsequently, the substrate may be repeatedly (once or more) anodized to grow the nanotube structures, soaked, and optionally heated to produce multiple antimicrobial layers within the surface structure. In some embodiments, the superficial surface of the substrate is modified with silver ions without further heating.

In some embodiments, the inventive method comprises forming one or more additional antimicrobial oxide layers in addition to the first and second antimicrobial oxide layers. Any additional oxide layer(s) may be comprised of the same, or a different material than the first and second antimicrobial oxide layer. In some embodiments, at least one of one or more additional antimicrobial oxide layers present is contained within nanostructures that are disposed on the metal surface.

In some embodiments, the inventive method comprises forming on the antimicrobial medical device (e.g., on the metal surface) a ceramic layer (e.g., calcium phosphate). In some embodiments, the ceramic layer comprises an antimicrobial material. For example, in some embodiments, the ceramic layer comprises atoms of an antimicrobial metal selected from the group consisting of silver, copper, and zinc, and combinations thereof.

In some embodiments, the inventive method comprises forming, on the first antimicrobial oxide layer, in a direction opposite that of that of the metal surface, an intermediate layer. In some embodiments, the intermediate layer is formed between the first and second antimicrobial oxide layers.

While the intermediate layer may be formed using any art-acceptable method, in some embodiments, the intermediate layer is spray-coated on the substrate (e.g., onto the metal surface or first antimicrobial oxide layer), or is formed using physical vapor deposition (PVD).

In some embodiments, the inventive method comprises disposing the metal surface of the antimicrobial medical device on a three-dimensional structure, such as an implant. As used in this context, the metal surface would be considered to be disposed on the structure regardless of whether the structure is first provided and the metal surface is formed thereon, or whether the metal surface is formed, and the structure is thereafter formed thereunder. In some embodiments, the method comprises forming the metal surface, and thereafter joining the three-dimensional structure to the metal surface. For example, in some embodiments, the inventive method comprises injection molding a three-dimensional structure (e.g., the body of an implant) to the metal surface. In some embodiments, the three-dimensional structure comprises a metallic, ceramic, stainless steel, polymeric (e.g., polyether-ether-ketone (PEEK)), or other material.

EXAMPLES

The invention will now be illustrated, but not limited, by reference to the specific embodiments described in the following examples.

Figure 2:
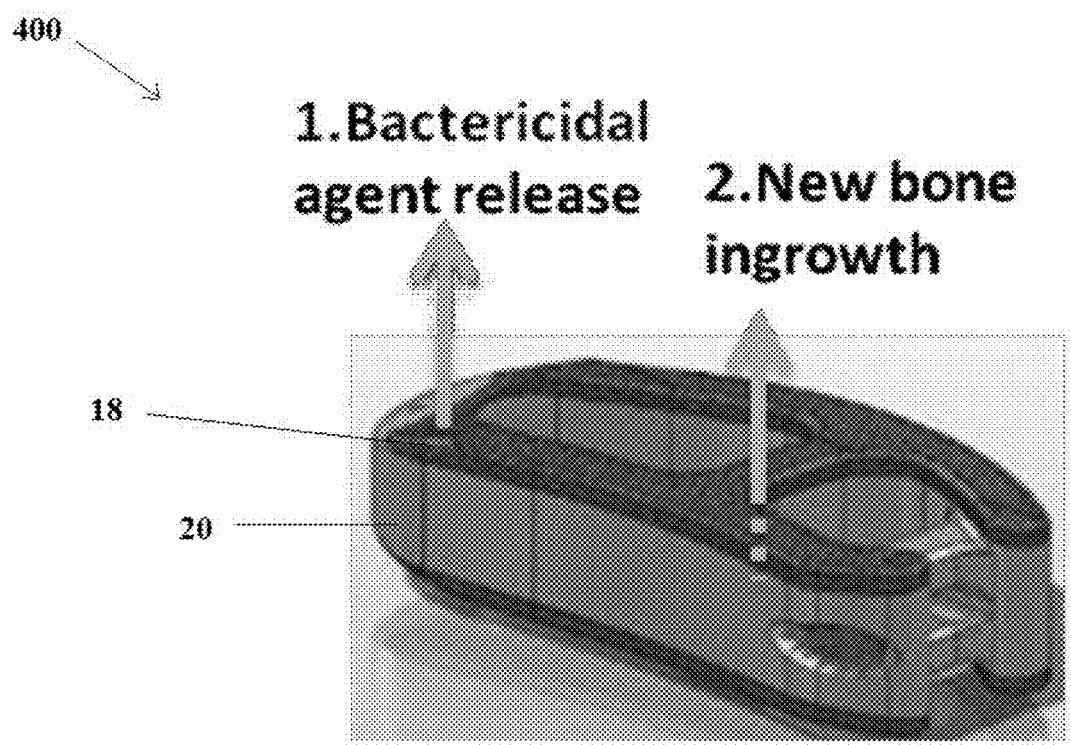
FIG. 2 depicts an embodiment of the inventive antimicrobial medical device.

Example 1: Interbody Fusion Device (IFD) Having an Antimicrobial Osteoinductive Nanotube Surface A sustained-release of bacteria-reducing ions was developed on an osteoinductive nanotube surface platform applied to a porous titanium scaffold-PEEK hybrid implant substrate, thereby forming antimicrobial IFD 400 as shown in FIG. 2. Specifically, the substrate was a porous titanium metal surface (Ti6Al4V), with PEEK 20 injection molded directly into the porous scaffold, thus resulting in an IFD with a very strong attachment strength to PEEK. Silver ion-comprising antimicrobial oxide layered titanium dioxide nanotubes (as depicted in FIG. 1B) were formed on the metal surface, thereby forming metal surface scaffold 18. Specifically, using a fluorine-containing electrolyte and low constant voltages, the IFD is treated to possess nanotubular structures. The anodization system is a two electrode circuit with titanium-containing part serving as an anode and a high purity platinum sheet (Alfa Aesar) as a cathode. The two electrodes are connected to a DC power supply and a constant voltage is applied during the anodization. During processing, the anode and cathode are kept with a separation distance of about 1 cm, and submerged into an electrolyte solution composed of dilute HF (0.5 wt %). The anodization voltage is adjusted from 3 to 25 V to produce nanotubes with increasing diameters. Next, a solution soaking method is used to allow silver ion exchange on the surface of the porous titanium scaffold. To do that, as-anodized titanium was soaked in an aqueous solution of $[Ag(NH_3)_2]NO_3$. To prepare the silver ammonia nitrate solution, droplets of ammonia hydroxide were added into 20 wt % silver nitrate until the precipitates all dissolved. The stock solution was further diluted to prepare 0.001M to 0.1 M working solutions. The soaking process lasted from 10 min to 24 hours and was either a one-time (single dose) or repeated (multiple dose). To do this, the substrates were rinsed with water thoroughly, completely dried in the air, and re-soaked in a silver containing solution. For the purpose of prolonged silver ion release, we tried more advanced methods to load the silver content.

The IFD leaves an open porous scaffold (i.e., the nanotubes) on the bone-opposing surface. Importantly, bone typically needs to grow only 300 microns into the antimicrobial osteo-integrative nanotube scaffold to achieve stability. For conventional implants, on the other hand, trabecular bone must grow through a distance of 5 to 16 mm, a process that typically takes 6 to 12 months or much longer (if ever), in the presence of surgical site infections. Accordingly, this and other embodiments of the inventive antimicrobial medical device are expected to achieve bone to implant fixation up to 80% faster than the standard of care, despite the presence of a surgical site infection. The IFD is able to maintain a release of a minimum inhibition concentration (MIC) to kill common bacteria strains observed in spinal implant infection for up to 2 weeks and is also able to control the speed and amount of released agents to minimize the toxicity of the ions, allowing the nanosurface morphology and surface energy advantages to increase osseointegration.

The IFD 400 provides a bone ingrowth scaffold that is 60-70% porous with interconnected pores that average 523 µm in diameter and would have very high attachment strength between the titanium scaffold and PEEK. IFD 400 is manufactured by diffusion bonding porous sheets together to create a three-dimensional porous structure. The porous sheets are typically etched with through holes to generate the porosity. After diffusion bonding, the scaffold may be milled, electric discharge machined, stamped, and/or formed to desired geometries. It can be diffusion bonded to titanium and cobalt chrome substrates and likewise, polymers such as PEEK are injection and/or compression molded into inserts to create polymer implants with titanium ingrowth regions. The strength of the mechanical bond between the PEEK and scaffold exceeds the 2900 psi strength requirement.

IFD 400 and other inventive embodiments are advantageous as compared to other substitute technologies such as plasma spray IFDs. Historically, plasma sprayed titanium has delaminated from PEEK, causing wear debris concerns whereas the novel injection molding approach provides very strong attachment of the scaffold to PEEK. Additionally, the best fixation strength possible for existing surfaces is determined by the limits of bone on growth to the surface of the IFD whereas inventive embodiments, including IFD 400, provide bone ingrowth into a scaffold. Literature on bone attachment strength to porous bone scaffolds, without further nanotube surface features and no infection suggests much higher attachment strength than simply rough surfaces. Trabecular metal implants come with similar porous structures but lack the desirable radiolucency and modulus offered by PEEK substrate.

The inventive multilayered antimicrobial surfaces, such as the nanotube surface on IFD 400, improve osseointegration to the implant surface. Optimized titanium nanotubular surface properties (including chemistry, morphology, wettability, etc.) can have significant effects on bone to implant fixation and therefore fixation and stability of the treated segment. The anodization technique used to form the nanotubes on IFD 400 can: (A) form a thin layer of titanium oxides on the surface which has been proven to be favored by bone cells; (B) incorporate hydroxyl groups so as to increase wettability to increase the adsorption of proteins known to decrease bacteria functions and increase bone cell functions; (C) create patterned nanostructures (specifically, nanotubes) uniformly over the surface, with controllable parameters (diameter, length, etc.) to direct bone cell functions; and (D) provide a good matrix for drug delivery, including the proposed ionic antibacterial agents (e.g., Ag+). The inventive layered and optionally nanostructured material constructs can be applied across all of divisions of orthopedics and neurosurgery that both treats infection and accelerates osseointegration and segmental stabilization despite SSI. Most importantly, this may all be accomplished without the use of drugs, since any drug has multiple effects in the body, not just the desired effect. The inventive embodiments also incorporate and stage the release of antimicrobial ions from the antimicrobial oxide layers on the metal surface so as to achieve rapid bone to implant fixation and segmental stabilization in both the absence and presence of infection.

Example 2: 3D Titanium Porous Scaffold onto PEEK Substrate—Animal Study

Figure 3:
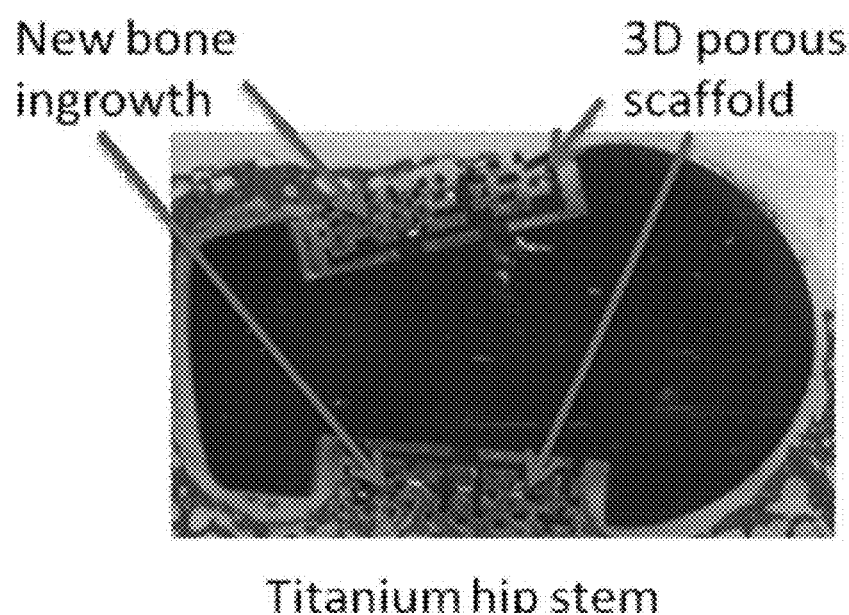
FIG. 3 is an image of a histological section of titanium hip step in accordance with an embodiment of the invention with 3D porous scaffold.

By diffusion bonding CAD designed porous titanium sheets together, 3D porous scaffolds with a thickness of around 1 mm are created. PEEK cages are compression molded into inserts to create a composite IFD with titanium ingrowth regions on both sides. The 3D scaffold is studied in a dog tibia model (see FIG. 3) and it is found that the fraction of available void space filled with bone and tissue after 12 weeks was 0.754 ($\sigma$=0.093). This preliminary animal study shows the average bone ingrowth for fiber titanium is reported to range from 0.23-0.38 in a 12 week study using a canine THR model.

Example 3: Pedicle Screws with Nanotubes 30 nm in Diameter

Figure 4A:
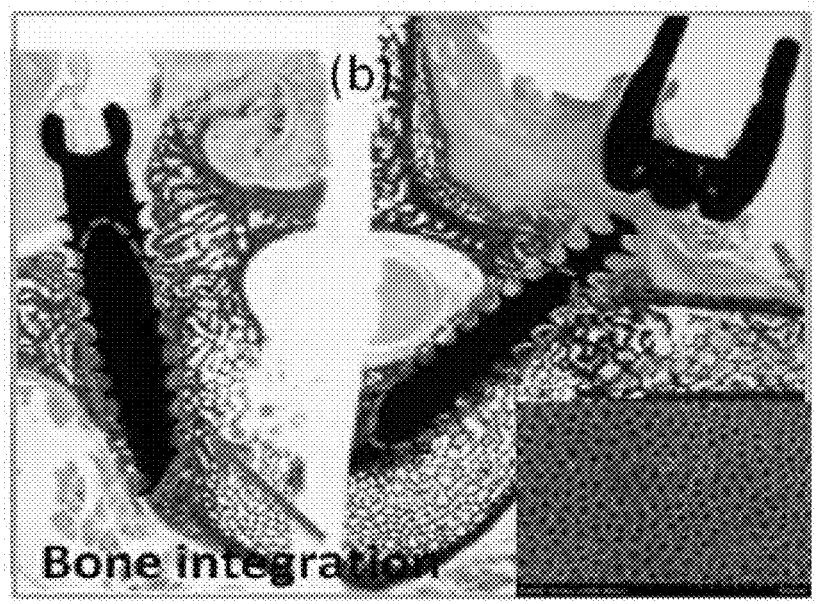
FIG. 4A depicts pedicle screws in accordance with an embodiment of the present invention.
Figure 4B:
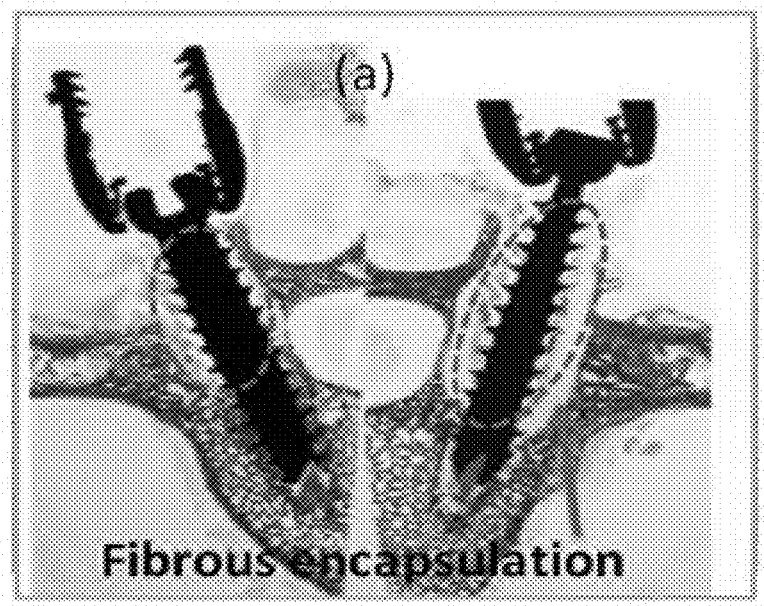
FIG. 4B depicts comparative prior art pedicle screws not in accordance with an embodiment of the present invention.

FIG. 4A depicts anodized titanium pedicle screws with nanotubes 30 nm in diameter in sheep pedicles after 3 months. The screws are titanium screws that were anodized to form titanium dioxide nanotubes with antimicrobial oxide layers formed therein, as described in Example 1, above. FIG. 4B depicts titanium pedicle screws without any nanotubes and antimicrobial oxide layers formed therein. As can be seen by comparing FIGS. 4A and 4B, use of the inventive embodiment significantly reduced screw loosening compared to conventional screws.

Figure 5:
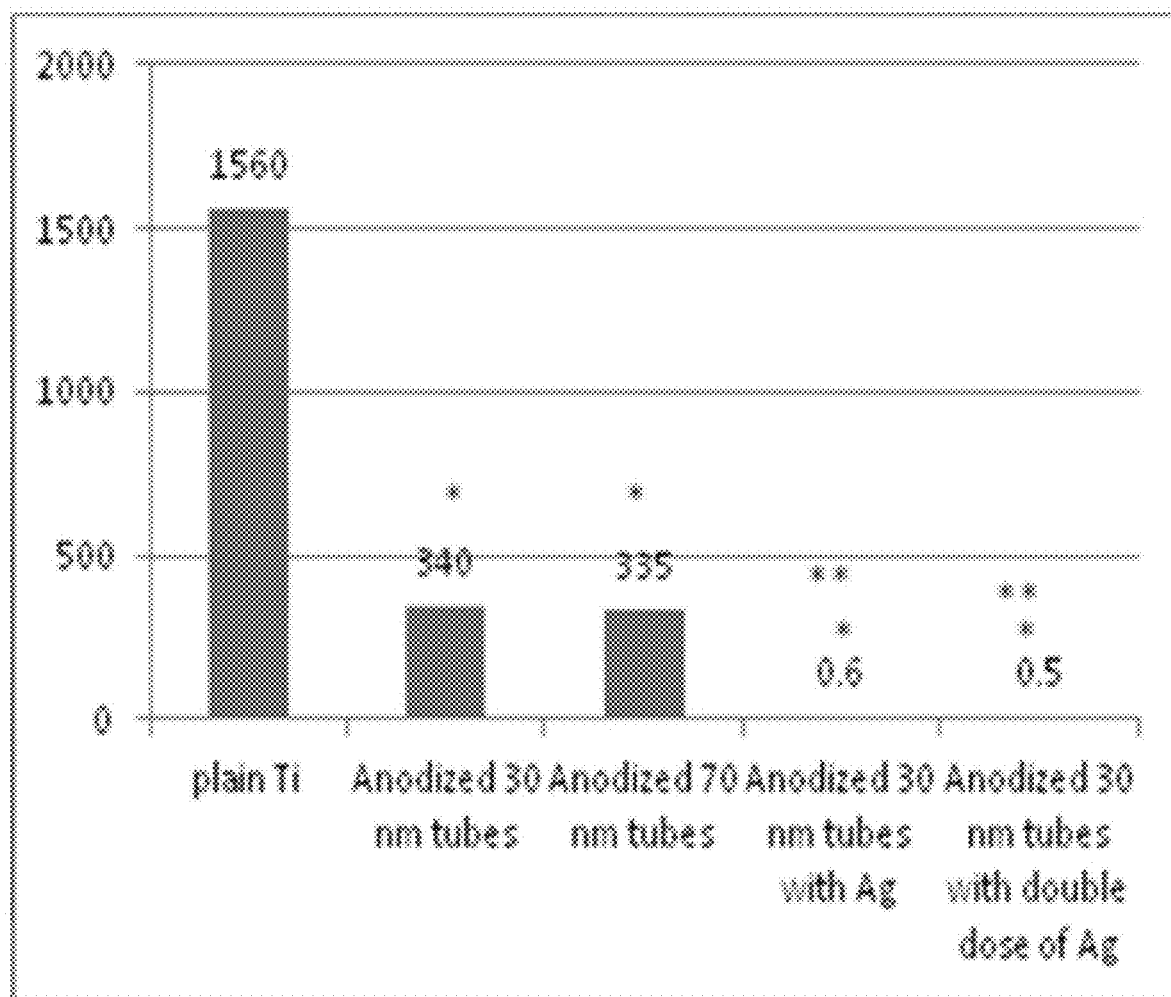
FIG. 5 provides a chart showing data for *S. aureus* colony forming units on various Ti rods inserted into the skin of guinea pigs in accordance with controls and techniques used according to embodiments of the invention.

Example 4: Efficacy of Silver Loaded Nanotubular Titanium on Reducing Bacteria Growth Two full-thickness incisions, 0.5-cm apart were created on the skin of guinea pigs. Various titanium wires (consisting of controls (no modification) ("plain Ti" in FIG. 5), anodized to possess nanotubes ("Anodized 30 nm tubes" and "Anodized 70 nm tubes" in FIG. 5) and anodized to possess nanotubes having a first antimicrobial oxide layer ("Anodized 30 nm tubes with Ag and "Anodized 30 nm tubes with double dose of Ag) were separately inserted into the wound site. For the bacteria challenge study group, the surgical sites (insertion and exit site) in half of the animals receiving implants were randomly inoculated with a standard aliquot of $1\times10^6$ S. aureus (ATCC, strain no. 29213). Dorsal skin sections containing the rods were harvested 7 days after implantation and biofilm analyzed for colony forming unit by sonication at 50 Hz for 7 min followed by agar. Experiments were conducted in triplicate. FIG. 5 provides a chart that summarizes the results, which evidence decreased S. aureus growth when using anodized titanium coated with Ag ions compared to anodized titanium alone or plain titanium. A $\frac{1}{5}^{th}$ and a 5 log reduction was found when using anodized Ti alone and anodized Ti with Ag ions, respectively. In FIG. 5, Data=mean+−SEM; N=3; * p<0.01 compared to plain titanium and ** p<0.01 compared to anodized titanium alone. Y axis is colony forming units×106. Ti was anodized at 10 or 20 V and then soaked in 0.001M [Ag(NH3)2]NO3 for 30 or 60 minutes (double dose).

Example 5: Inventive Embodiments Have Acceptable Cytotoxicity

Figure 6:
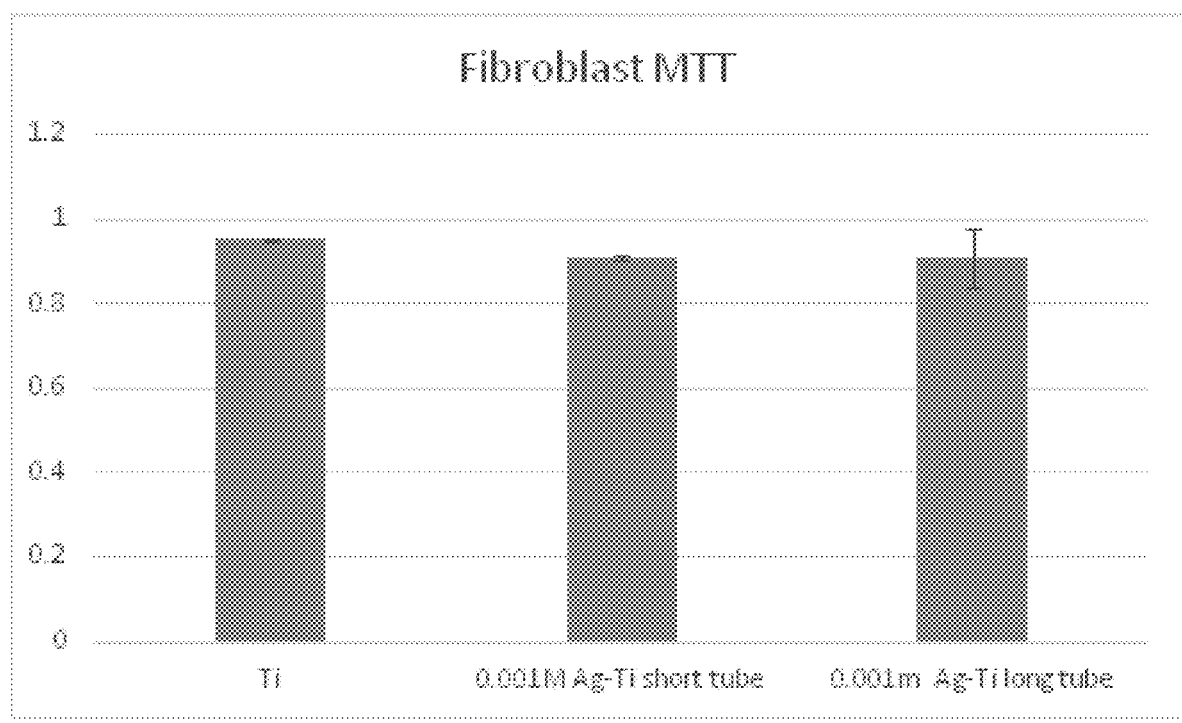
FIG. 6 is a bar-graph showing standard human fibroblast cytotoxicity of matrices treated with antimicrobial agents commensurate with embodiments of the present invention.

FIG. 6 is a bar-graph showing standard human fibroblast cytotoxicity of matrices treated with antimicrobial agents commensurate with embodiments of the present invention. Anodized Ti-6Al-4V either was not silver-loaded or was (i) anodized in 0.5% HF solution for 10 min at 20V to form short nanotubes, (ii) anodized in 0.5% HF/16.7 $H_2O$/DMSO solution for 2 hours at 40 volts to form long nanotubes, and then silver-loaded by being soaked in 0.001M [Ag($NH_3$)$_2$]$NO_3$ for 30 minutes. Extracts from individual samples after 24 h soaking were added into a pre-cultured fibroblast plate and the proliferation of human fibroblast was then measured using standard MTT assay as shown on the Y-axis in arbitrary units in FIG. 6. As can be seen, human fibroblasts growth exposed to extracts from anodized Ti-6Al-4V soaked in 0.001M solution for 30 minutes, with varied nanotube thickness, were equivalent to that on non-silver-loaded surface, thus demonstrating acceptable cytotoxicity for the inventive embodiments.

Example 6: Inventive Embodiments Have Acceptable Cytotoxicity

Figure 7A:
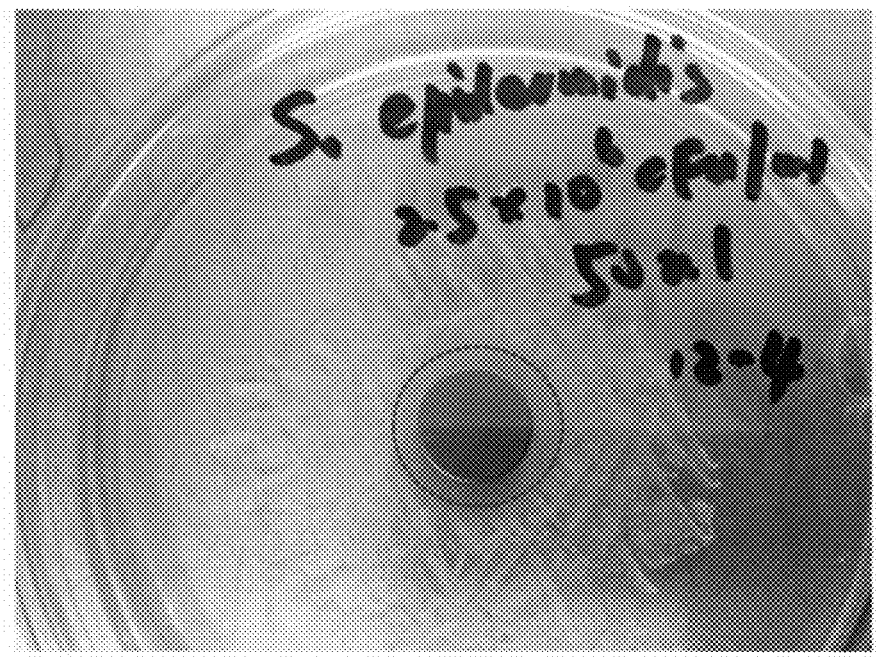
FIGS. 7A and 7B show the effect of antimicrobial agents used in embodiments of the present invention on inhibition of *Staphylococcus epidermidis* and *Pseudomonas aeruginosa* growth.
Figure 7B:
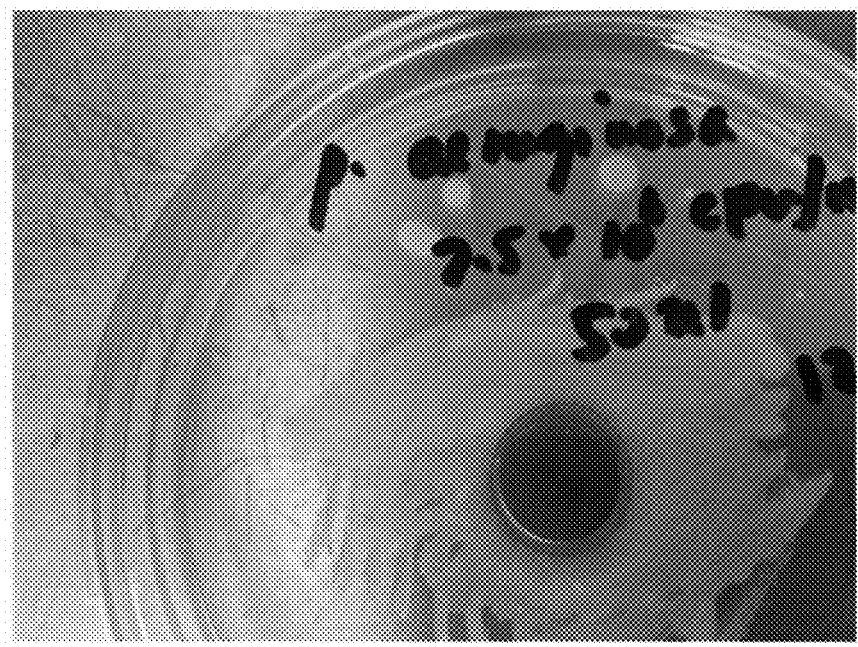

FIGS. 7A and 7B show the effect of antimicrobial agents used in embodiments of the present invention (namely, silver ions) on inhibition of *Staphylococcus epidermidis* and *Pseudomonas aeruginosa* growth. For this example, Ti-6Al-4V was anodized in an HF solution then soaked for approximately 30 minutes in an 0.001M [Ag($NH_3$)$_2$]$NO_3$ solution. 50 ul of each bacteria strain at a concentration of $2.5\times10^6$ cfu/ml was inoculated onto an agar plate S. with the silver-loaded sample on top of it. As see in FIG. 7A (for *Staphylococcus epidermidis*) and 7B (for the *Pseudomonas aeruginosa*), after 24 hours an inhibition zone appeared for both bacteria strains.

Example 7: Structural and Chemical Analysis of Anodized Ti-6Al-4V Treated with Silver Solution FIGS. 8A-C provide SEM and EDS image data relating to structural features and the chemical makeup of a nanofunctionalized device according to methods discussed herein, having a first antimicrobial oxide layer. For this example, a Ti-6Al-4V metal surface was anodized in a 0.5% solution of HF for 10 minutes at 10 V. Following anodization, the object was soaked in 0.001M [Ag($NH_3$)$_2$]$NO_3$ for 30 minutes, then dried. The micro and nanoscale surface features of the device were then imaged by scanning electron microscopy (SEM), and the elemental composition of the surface determined by energy dispersive spectrometry (EDS). Microscopy and spectrometry were conducted according to standard methods which would be known to ordinarily skilled artisans. The images shown in FIGS. 8A and 8B are SEM images at 20K magnification and 150K magnification, respectively. The formation of nanotubular structures on the matrix of the object can be seen at higher magnification (FIG. 8B). FIG. 8C provides an EDS spectrum that shows emissions characteristic of elemental silver, indicating the adsorption of silver (wt % ranging from 1 to 4%, i.e., of 100 grams of atoms on the surface, 1 to 4 would be silver) onto device so as to form at least the first antimicrobial oxide layer. The highest peak, at approximately 4.5 keV, represents elemental titanium.

Example 8: Effects of Different Anodization and Soaking Regimens

Figure 9:
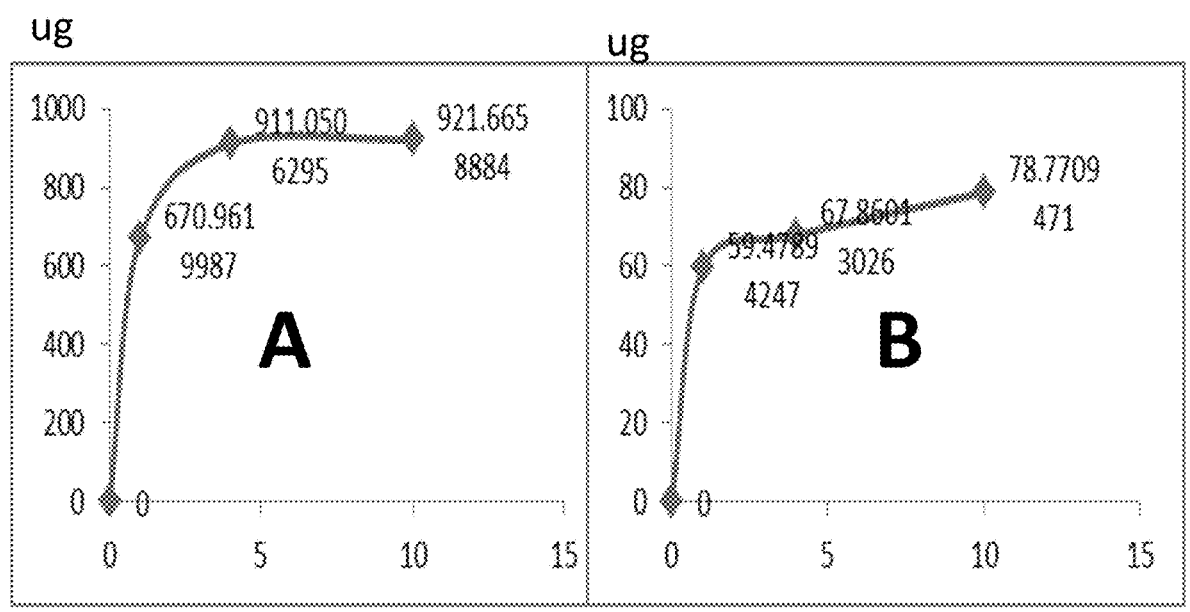
FIG. 9 provides line graphs that demonstrate the effects of different anodization and soaking regimens on the amount and duration of antimicrobial release from a treated matrix.

The line graphs of FIG. 9 demonstrate the effects of different anodization and soaking regimens on the amount and duration of antimicrobial release from a treated matrix. For these examples, discs of Ti-6Al-4V were anodized in an HF solution as described above, then soaked in 0.01M [Ag(NH$_3$)$_2$]NO$_3$. Silver release from the discs was then measured, as shown on the Y-axis, over a period of twelve (12) days, as shown on the X-axis. Graph A shows release behavior of a disc that was anodized once then repeatedly soaked in 0.01M [Ag(NH$_3$)$_2$]NO$_3$. As can be seen, there was a burst of silver release on day 1 from a disc receiving this treatment, and most of the silver had been released by day 4. Graph B, by comparison, shows release behavior of a disc that was, sequentially, anodized as described, soaked as described, again anodized, then again soaked, so as to form first and second antimicrobial oxide layers. As can be seen, this repeated alternation between anodization and soaking resulted in more prolonged release of silver and less concentrated levels of release.

Example 9: Bactericidal Effect of Treating Matrices with Silver Solutions as Described Herein FIGS. 10A and 10B are photomicrographs that show *S. sureus* growth on anodized Ti-6Al-4V in the absence of antimicrobial treatment (control) (FIG. 10A) and on anodized Ti-6Al-4V that has been soaked for approximately 30 minutes in an [Ag(NH$_3$)$_2$]NO$_3$ solution (FIG. 10B). For this example, Ti-6Al-4V was anodized in an HF solution then soaked for approximately 30 minutes in an [Ag(NH$_3$)$_2$]NO$_3$ solution (FIG. 10B) and dried as described above or not soaked in [Ag(NH$_3$)$_2$]NO$_3$ (FIG. 10A). *S. sureus* was then cultured on the surfaces. As see in FIG. 10B, after four (4) hours, few colonies survived on the surface that had been soaked in [Ag(NH$_3$)$_2$]NO$_3$, indicating the bactericidal effect of treating matrices with solutions as described herein. On the other hand, FIG. 10A shows growth of significant colonies.

Figure 11:
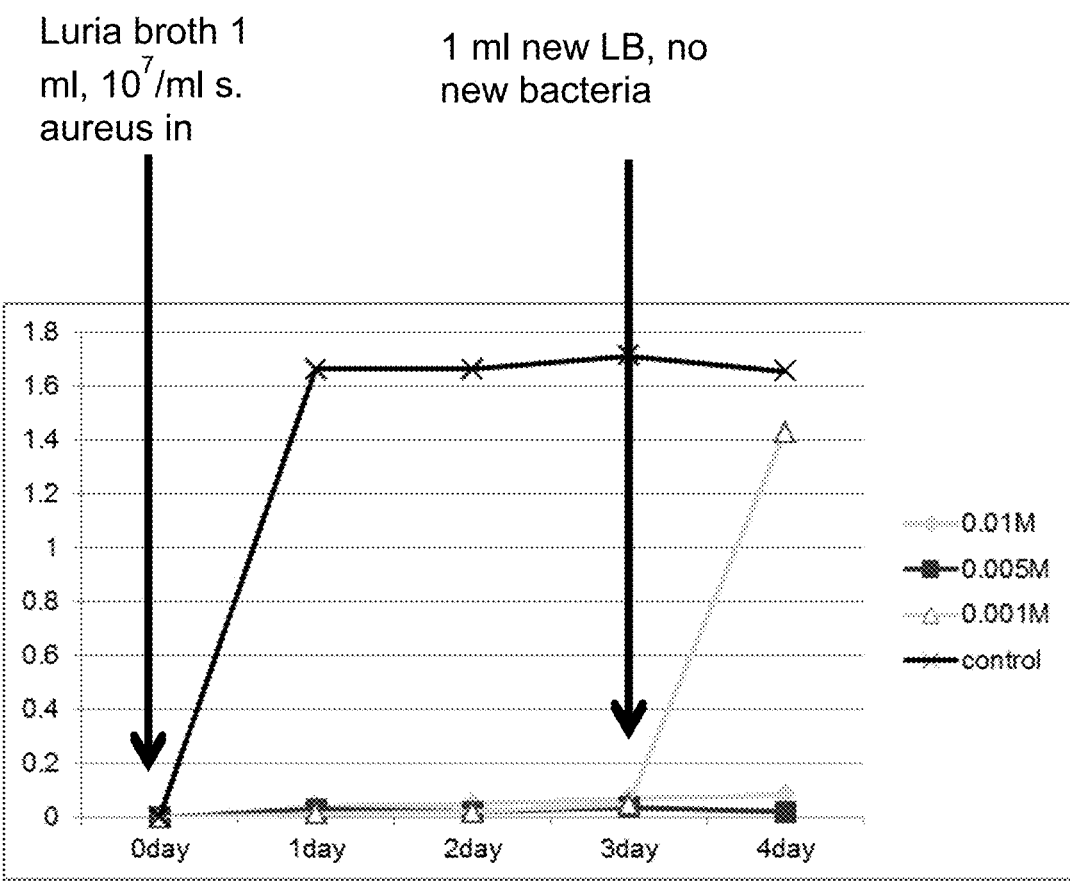
FIG. 11 is a line graph showing durations of bactericidal effect of device matrices treated with antimicrobial oxide layers described herein depending on the concentration of bactericidal solution in which they had been soaked during treatment.

Example 10: Durations of Bactericidal Effect of Treated Devices with Antimicrobial Oxide Layers The line-graph in FIG. 11 shows durations of bactericidal effect of device matrices treated with antimicrobial oxide layers described herein depending on the concentration of bactericidal solution in which they had been soaked during treatment. The Y-axis shows bacterial growth in arbitrary units, measured over several days, as shown on the X-axis. For this example, Ti-6Al-4V discs were anodized for 10 minutes in a 0.5% HF solution, then ionic silver-loaded by incubation for 30 minutes in a solution containing the indicated concentrations of [Ag(NH$_3$)$_2$]NO$_3$. The control was not incubated in [Ag(NH$_3$)$_2$]NO$_3$. Discs were then placed in culture wells, then challenged once with 1 ml of Luria broth containing 10$^7$/ml *S. aureus*, as shown in FIG. 11. Note that this concentration of *S. aureus* is much higher than a more physiologically relevant concentration such as approximately 10$^4$/ml. As can be seen in FIG. 11, the control substrate permitted bacterial growth from day 1 while all silver-loaded substrates inhibited bacterial growth up to three (3) days; growth in the lowest concentration sample was seen on day 4 due to exhausted silver release.

Figure 12:
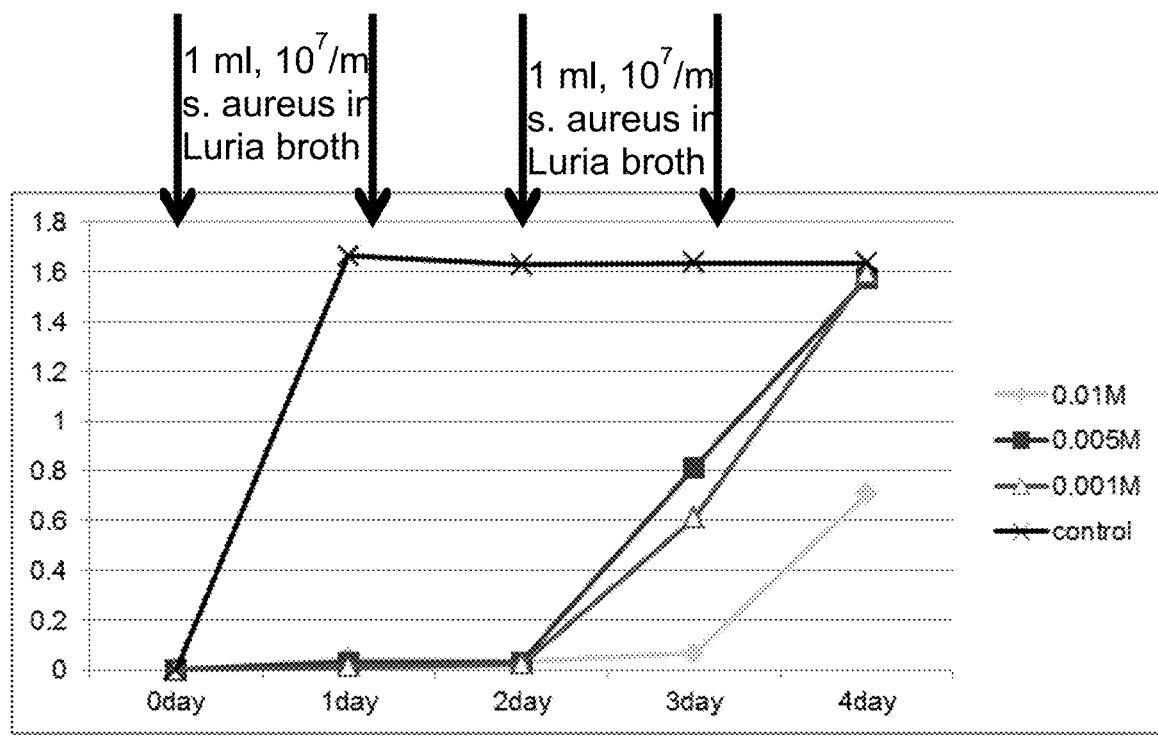
FIG. 12 is a line graph showing durations of bactericidal effect of device matrices treated with antimicrobial oxide layers described herein depending on the concentration of bactericidal solution in which they had been soaked during treatment, upon continual presentation with a bacterial challenge.

FIG. 12 is a line graph showing durations of bactericidal effect of device matrices treated with antimicrobial oxide layers described herein depending on the concentration of bactericidal solution in which they had been soaked during treatment, upon continual presentation with a bacterial challenge. The Y-axis shows bacterial growth in arbitrary units, measured over several days, as shown on the X-axis. For this example, Ti-6Al-4V discs were anodized for 10 minutes in a 0.5% HF solution, then ionic silver-loaded by incubation for approximately 30 minutes in a solution containing the indicated concentrations of [Ag(NH$_3$)$_2$]NO$_3$. The control was not incubated in [Ag(NH$_3$)$_2$]NO$_3$. Discs were then placed in culture wells, then challenged with 1 ml of Luria broth containing 10$^7$/ml *S. aureus* every day for four consecutive days, as shown in FIG. 12. As can be seen in FIG. 12, the control substrate permitted bacterial growth from day 1, while all silver-loaded substrates inhibited bacterial growth up to three (3) days or more even after repeated daily inoculation with fresh bacterial stock; growth in the lower concentration samples began to be seen on day 3, and in the highest concentration sample growth began to be seen on day 4, due to exhausted silver release.

Example 11: Bone Growth on Device Matrices Treated with Silver

Figure 13:
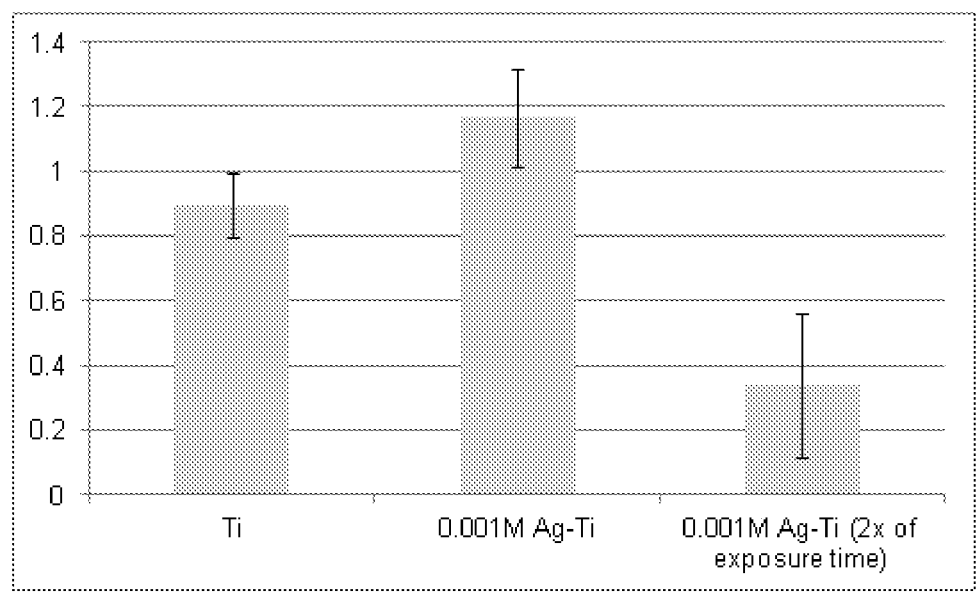
FIG. 13 is a bar-graph depicting bone growth on device matrices treated with antimicrobial agent.

FIG. 13 is a bar-graph depicting bone growth on device matrices treated with antimicrobial agent. For this example, anodized Ti-6Al-4V either was not silver-loaded or was silver-loaded by being soaked in 0.001M [Ag(NH$_3$)$_2$]NO$_3$. Soaking duration was for either 30 minutes or 60 minutes. Proliferation of human osteoblasts on treated surfaces was then measured, as shown on the Y-axis in arbitrary units in FIG. 13. The left bar in FIG. 13 shows proliferation on non-silver-loaded matrices, the middle bar shows proliferation on matrices that were silver-loaded by soaking in 0.001M [Ag(NH$_3$)$_2$]NO$_3$ for 30 minutes, and the bar on the right shows proliferation on matrices that were silver-loaded by soaking in 0.001M [Ag(NH$_3$)$_2$]NO$_3$ for 60 minutes. As can be seen in FIG. 13, bone cell growth on anodized Ti-6Al-4V soaked in 0.001M solution for 30 minutes was equivalent to that on non-silver-loaded surface, while increasing silver content on the matrix through prolonged soaking time can reduce bone cell growth. Embodiments of the present invention allow for the avoidance of such bone growth detriment, through controlled sustained antimicrobial agent release via the inventive multi-layering approach.

Figure 14:
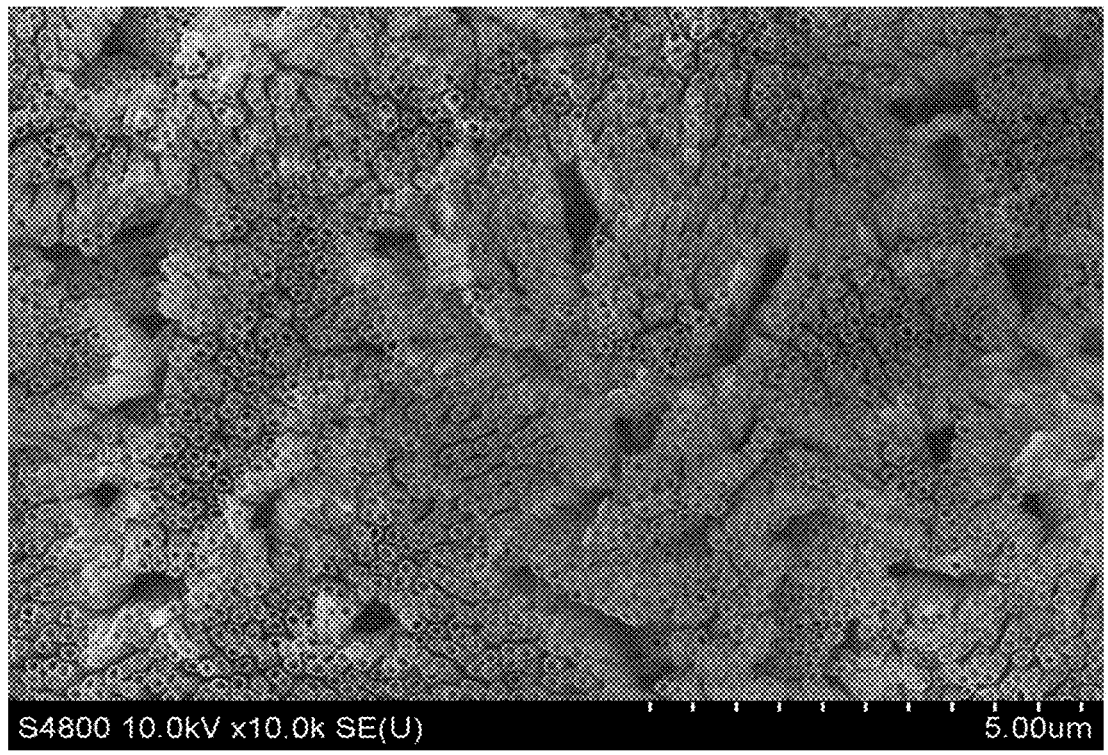
FIG. 14 is an SEM image of anodized titanium alloy Ti-6Al-4V.

Example 12: Modification of Nanostructures that may be Used in Embodiments of the Invention FIG. 14 is an SEM of titanium alloy Ti-6Al-4V anodized, for example, in 0.5% HF/16.7 H$_2$O/DMSO solution for 2 hours at 40 volts and treated with 0.001M [Ag(NH$_3$)$_2$]NO$_3$ for 30 minutes. As will be readily appreciated by persons having ordinary skill in the art, the tube size, length, and inter-tube space can be modified by using different parameters. Specifically, the anodization parameters, including voltage, current density, duration, electrolyte composition, pH, and temperature, may be controlled to customize the length, tube size, and inter-tube spacing of the nanotube structures which in turn influence the loading and releasing of silver ions. For example, increasing the voltage may increase tube size and inter-tubular spacing and increasing voltage duration may increase tube structure length.

Figure 15:
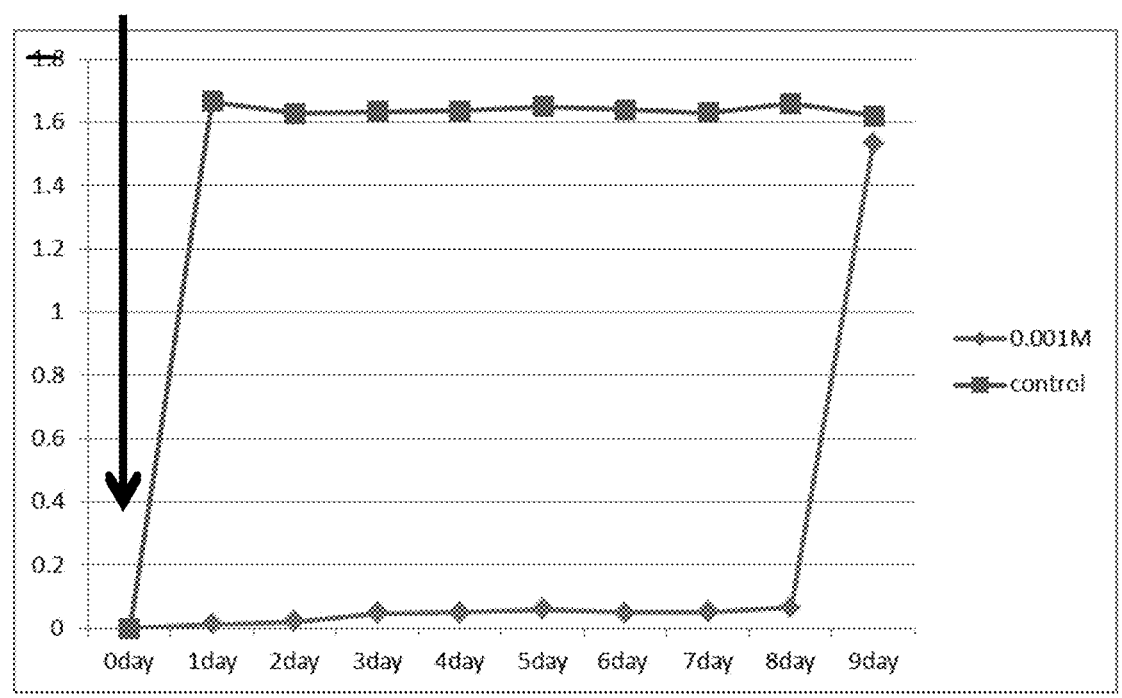
FIG. 15 is a line graph showing results of Ti-6Al-4V anodized under different conditions.

For example, as seen in FIG. 15, a line graph shows the results of when Ti-6Al-4V is anodized in 16.7% water/DMSO/0.5% HF electrolyte under 40 volts for 2 hours at 50 degrees C. and loaded with silver ions by single time soaking in 0.001M [Ag(NH$_3$)$_2$]NO$_3$ for 30 minutes. The resultant matrix inhibits *S. aureus* growth up to 8 days compared to 3 days of Ti-6Al-4V anodized in water/0.5% HF electrolyte under 10 volts for 10 minutes and loaded with silver ions by single time soaking in 0.001M [Ag(NH$_3$)$_2$]NO$_3$ for 30 minutes. The increased inhibition period is considered a result of increased amount of Ag ions loaded into the nanotubes which have larger size, length and interspaces than Ti-6Al-4V anodized in water/0.5% HF electrolyte under 10 volts for 10 minutes.

Figure 16:
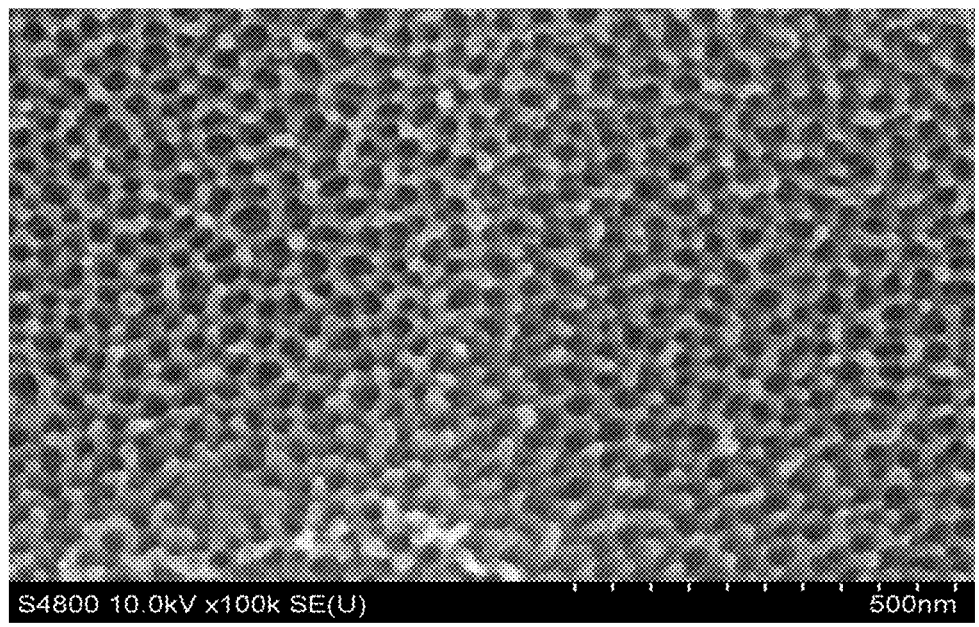
FIG. 16 shows an SEM image of titanium alloy Ti-6Al-4V that includes a ceramic layer loaded with antimicrobial silver ions.

Example 13: Antimicrobial Medical Device Comprising a Ceramic Antimicrobial Loaded Layer A further embodiment of the invention includes a medical device comprising a ceramic layer (e.g., calcium phosphate). In some embodiments, the ceramic layer comprises atoms of an antimicrobial metal selected from the group consisting of silver, copper, and zinc, and combinations thereof. FIG. 16 shows an SEM image of titanium alloy Ti-6Al-4V, which was ultimately anodized in 0.5% HF solution for 10 minutes at 10 volts, then coated with calcium phosphate using an electro-deposition process, and finally treated with 0.001M [Ag(NH$_3$)$_2$]NO$_3$ for 30 minutes, thereby resulting of loading of silver ions into the ceramic. In various embodiments, the first and second antimicrobial oxide layers are formed below the ceramic layer (i.e., between the metal surface and the ceramic layer).

Figure 17:
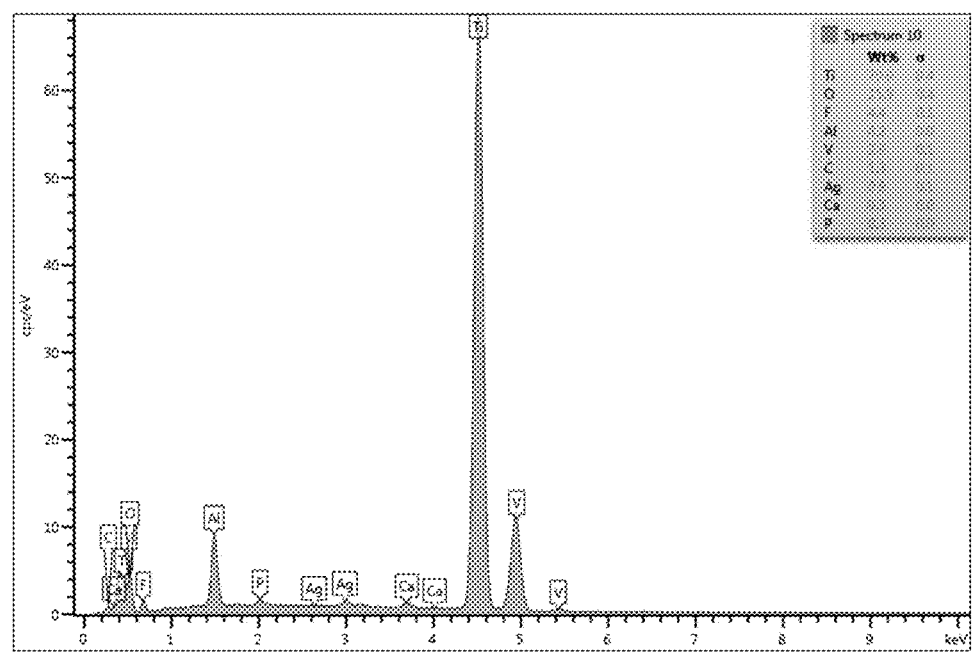
FIG. 17 is graph of the spectrum of surface chemistry of an anodized titanium alloy surface coated with calcium phosphate.

FIG. 17 is a spectrum of surface chemistry by EDS which indicates the existence of calcium phosphate and incorporation of silver ions into the ceramic. In addition, the nanostructures formed during anodization of the Ti-6Al-4V were also all covered by the calcium phosphate.

Figure 18:
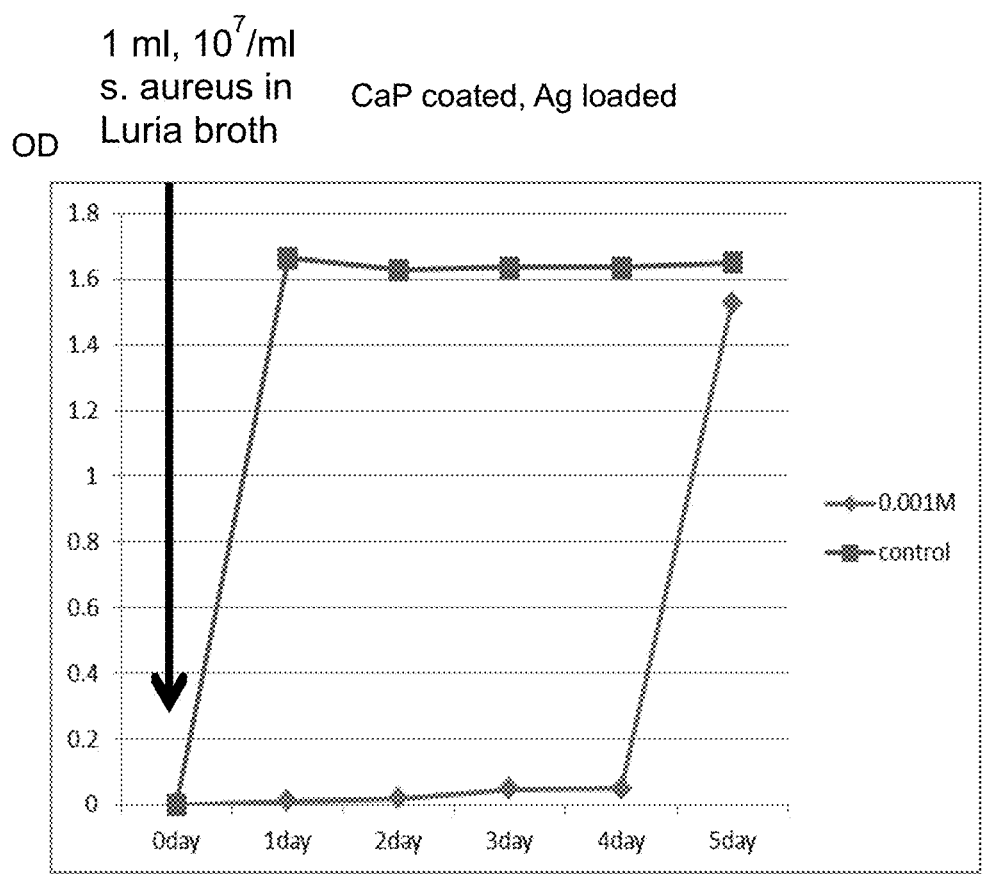
FIG. 18 is a line-graph showing bacterial growth in a culture well containing a Ti-6Al-4V sample (control) and a silver loaded calcium phosphate coated anodized Ti-6Al-4V disc.

FIG. 18 is a line graph that shows *S. aureus* growth in a culture well containing a Ti-6Al-4V sample (control) and the silver loaded calcium phosphate coated Ti-6Al-4V disc of the present example. The Y-axis is arbitrary units. Note that the 10$^7$/ml seeding density appears to be much more than physiological relevant value ~10$^4$/ml. The control substrate has bacteria growth from day 1 reaching a detecting limit while the silver loaded calcium phosphate coated substrate inhibited bacteria growth up to 4 days.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:

1. An antimicrobial medical device comprising:
    a substrate comprising a metal surface, said metal surface comprising atoms of at least one of a metal or metal alloy comprising one or more of stainless steel, cobalt, and titanium;
    wherein on the metal surface, a first antimicrobial oxide layer comprising atoms of the metal or metal alloy and atoms of an antimicrobial metal selected from the group consisting of silver, copper, and zinc, and combinations thereof, the atoms of antimicrobial metal being present in the first antimicrobial oxide layer in a first concentration, said first antimicrobial oxide layer having a thickness of 100 nm to 800 nm;
    wherein on the first antimicrobial oxide layer, positioned in a direction opposite that of the metal surface, a second antimicrobial oxide layer comprising atoms of an antimicrobial metal selected from the group consisting of silver, copper, and zinc, and combinations thereof, the atoms of antimicrobial metal being present in the second antimicrobial oxide layer in a second concentration, said second antimicrobial oxide layer having a thickness of 100 nm to 800 nm; and wherein the first concentration is not equal to the second concentration, and wherein the device comprises a plurality of nanostructures, and the first and/or second antimicrobial oxide layer is contained within the plurality of nanostructures.

2. The antimicrobial medical device according to claim 1, wherein the oxide in the second antimicrobial oxide layer comprises silver atoms.

3. The antimicrobial medical device according to claim 1, wherein the oxide in the second antimicrobial oxide layer comprises atoms of at least one of stainless steel, cobalt, and titanium.

4. The antimicrobial medical device according to claim 1, wherein the first and second antimicrobial oxide layers are in direct contact with one another.

5. The antimicrobial medical device according to claim 1, wherein the first concentration is greater than the second concentration.

6. The antimicrobial medical device according to claim 1, wherein the first concentration is less than the second concentration.

7. The antimicrobial medical device according to claim 1, wherein the first antimicrobial oxide layer comprises silver atoms.

8. The antimicrobial medical device according to claim 1, wherein the device is selected from an orthopedic implant and a neurosurgical implant.

9. The antimicrobial medical device according to claim 1, wherein the first and second antimicrobial oxide layers are distinct layers separated from one another by at least an intermediate layer that does not comprise an antimicrobial metal selected from the group consisting of silver, copper, and zinc, and combinations thereof.

10. The antimicrobial medical device according to claim 9, wherein the intermediate layer comprises atoms of at least one of stainless steel, cobalt, and titanium.

11. The antimicrobial medical device according to claim 1, further comprising a ceramic layer, the ceramic layer comprising atoms of an antimicrobial metal selected from the group consisting of silver, copper, and zinc, and combinations thereof.

12. The antimicrobial medical device according to claim 11, wherein the ceramic layer comprises calcium phosphate.

13. The antimicrobial medical device according to claim 1, wherein the metal surface is fabricated from at least one of titanium, a titanium alloy, stainless steel, and a cobalt-chrome alloy.

14. The antimicrobial medical device according to claim 13, wherein the metal surface is selected from at least one of a Ti6Al4V and a cobalt-chrome alloy.

15. The antimicrobial medical device according to claim 14, wherein the metal surface is Ti6Al4V.

16. The antimicrobial medical device according to claim 1, wherein, during formation of the device, anodization takes place both before soaking to form the first antimicrobial layer and before soaking to form the second antimicrobial layer.

17. The antimicrobial medical device according to claim 16, wherein the nanostructures are nanotubes.

18. The antimicrobial medical device according to claim 16, wherein the nanostructures are amorphous non-crystalline nanostructures.

19. The antimicrobial medical device according to claim 18, wherein the nanostructures are titanium dioxide nanostructures.

20. The antimicrobial medical device according to claim 19, wherein the nanostructures are nanotubes.

21. The antimicrobial medical device according to claim 20, wherein the device is selected from an orthopedic implant and a neurosurgical implant.

22. A method for making an antimicrobial medical device according to claim 1, said method comprising:
providing a substrate comprising a metal surface, said metal surface comprising atoms of at least one of a metal or metal alloy comprising one or more of stainless steel, cobalt, and titanium;
forming, on the metal surface, a first antimicrobial oxide layer comprising atoms of the metal or metal alloy and atoms of an antimicrobial metal selected from the group consisting of silver, copper, and zinc, and combinations thereof, the atoms of antimicrobial metal being present in the first antimicrobial oxide layer in a first concentration; and
forming, on the first antimicrobial oxide layer, positioned in a direction opposite that of the metal surface, a second antimicrobial oxide layer comprising atoms of an antimicrobial metal selected from the group consisting of silver, copper, and zinc, and combinations thereof, the atoms of antimicrobial metal being present in the second antimicrobial oxide layer in a second concentration,
wherein the first concentration is not equal to the second concentration.

23. The method according to claim 22, wherein the first antimicrobial oxide layer comprises silver atoms.

24. The method according to claim 22, wherein forming the first antimicrobial oxide layer comprises heat treating the metal surface, acid etching the metal surface, or electrochemically oxidizing the metal surface.

25. The method according to claim 22, wherein forming the first antimicrobial oxide layer comprises anodizing the metal surface.

26. The method according to claim 22, wherein the plurality of nanostructures are formed by anodization.

27. The method according to claim 22, comprising forming one or more additional antimicrobial oxide layers in addition to the first and second antimicrobial oxide layers.

28. The method according to claim 22, further comprising:
forming, on the first antimicrobial oxide layer, in a direction opposite that of that of the metal surface, and between the first and second antimicrobial oxide layers, an intermediate layer that does not comprise an antimicrobial metal selected from the group consisting of silver, copper, and zinc, and combinations thereof, such that said first and second antimicrobial oxide layers are distinct layers separated from one another by at least the intermediate layer.

29. The method according to claim 22, wherein the antimicrobial medical device is selected from an orthopedic implant and a neurosurgical implant.

30. The method according to claim 22, wherein during formation of the device, anodization takes place both before soaking to form the first antimicrobial layer and before soaking to form the second antimicrobial layer.

31. The method according to claim 22, wherein at least one of forming the first antimicrobial oxide layer and forming the second antimicrobial oxide layer comprises exposing at least a portion of the device to a solution comprising an antimicrobial metal selected from the group consisting of silver, copper, and zinc, and combinations thereof, or to an antimicrobial metal ion thereof.

32. The method according to claim 31, wherein the solution comprises silver or silver ions.

33. The method according to claim 32, wherein the solution is an aqueous solution comprising $[Ag(NH_3)_2]NO_3$.

* * * * *